US009624477B2

(12) United States Patent
Cirpus et al.

(10) Patent No.: US 9,624,477 B2
(45) Date of Patent: *Apr. 18, 2017

(54) METHOD FOR PRODUCING UNSATURATED OMEGA-3-FATTY ACIDS IN TRANSGENIC ORGANISMS

(71) Applicant: BASF Plant Science GmbH, Ludwigshafen (DE)

(72) Inventors: Petra Cirpus, Mannheim (DE); Jörg Bauer, Teltow (DE); Thorsten Zank, Mannheim (DE); Ernst Heinz, Hamburg (DE)

(73) Assignee: BASF Plant Science GmbH, Ludwigshafen (DE)

( * ) Notice: Subject to any disclaimer, the term of this patent is extended or adjusted under 35 U.S.C. 154(b) by 391 days.

This patent is subject to a terminal disclaimer.

(21) Appl. No.: 13/737,513

(22) Filed: Jan. 9, 2013

(65) Prior Publication Data

US 2013/0116421 A1 May 9, 2013

Related U.S. Application Data

(62) Division of application No. 12/768,227, filed on Apr. 27, 2010, now Pat. No. 8,373,024, which is a division of application No. 10/590,958, filed as application No. PCT/EP2005/001865 on Feb. 23, 2005, now Pat. No. 7,777,098.

(30) Foreign Application Priority Data

Feb. 27, 2004 (DE) ......................... 10 2004 009 458

(51) Int. Cl.
C12N 15/82 (2006.01)
C12N 9/02 (2006.01)

(52) U.S. Cl.
CPC ......... *C12N 9/0071* (2013.01); *C12N 9/0004* (2013.01); *C12N 15/8247* (2013.01)

(58) Field of Classification Search
None
See application file for complete search history.

(56) References Cited

U.S. PATENT DOCUMENTS

| | | | |
|---|---|---|---|
| 5,614,393 A | 3/1997 | Thomas et al. | |
| 6,043,411 A | 3/2000 | Nishizawa et al. | |
| 6,459,018 B1 * | 10/2002 | Knutzon | 800/281 |
| 6,884,921 B2 | 4/2005 | Browse et al. | |
| 7,777,098 B2 | 8/2010 | Cirpus et al. | |
| 2004/0049805 A1 | 3/2004 | Lerchl et al. | |
| 2004/0053379 A1 | 3/2004 | Lerchl et al. | |
| 2004/0111763 A1 | 6/2004 | Heinz et al. | |
| 2004/0172682 A1 | 9/2004 | Kinney et al. | |
| 2008/0076164 A1 | 3/2008 | Cirpus et al. | |
| 2008/0155705 A1 | 6/2008 | Zank et al. | |
| 2009/0222951 A1 | 9/2009 | Cirpus et al. | |
| 2010/0021976 A1 | 1/2010 | Lerchl et al. | |
| 2013/0116421 A1 | 5/2013 | Cirpus et al. | |

FOREIGN PATENT DOCUMENTS

| | | |
|---|---|---|
| AU | 2001239244 B2 | 8/2001 |
| AU | 2003232512 B2 | 11/2003 |
| AU | 2003258496 A1 | 1/2004 |
| AU | 2004215705 B2 | 9/2004 |
| AU | 2004225838 B2 | 10/2004 |
| AU | 2004227075 B8 | 10/2004 |
| AU | 2005217080 B2 | 9/2005 |
| CA | 2 485 060 | 11/2003 |
| DE | 101 02 337 A1 | 7/2002 |
| DE | 102 19 203 | 11/2003 |
| EP | 0 550 162 A1 | 7/1993 |
| EP | 0 794 250 A1 | 9/1997 |
| WO | WO-91/13972 | 9/1991 |
| WO | WO-93/06712 | 4/1993 |
| WO | WO-93/11245 | 6/1993 |
| WO | WO-94/11516 | 5/1994 |
| WO | WO-94/18337 | 8/1994 |
| WO | WO-95/18222 | 7/1995 |
| WO | WO-96/21022 | 7/1996 |
| WO | WO-97/21340 | 6/1997 |
| WO | WO-97/30582 | 8/1997 |
| WO | WO-98/46763 | 10/1998 |
| WO | WO-98/46764 A1 | 10/1998 |
| WO | WO-98/46765 | 10/1998 |
| WO | WO-98/46776 | 10/1998 |

(Continued)

OTHER PUBLICATIONS

Abbadi, A. et al., "Biosynthesis of Very-Long-Chain Polyunsaturated Fatty Acids in Transgenic Oilseeds: Constraints on Their Accumulation", The Plant Cell 16 (2004), pp. 2734-2748.
Akimoto, M. et al., "Carbon Dioxide Fixation and Polyunsaturated Fatty Acid Production by the Red Alga *Porphyridium cruenturn*", Applied Biochemistry and Biotechnology 73 (1998), pp. 269-278.
Calder, P.C., "Dietary Modification of Inflammation with Lipids", Proceedings of the Nutrition Society 61 (2002), pp. 345-358.
Cleland, L.G. et al., "Fish Oil and Rheumatoid Arthritis: Antiinflammatory and Collateral Health Benefits", The Journal of Rheumatology, 27:10 (2000), pp. 2305-2307.
Chalova, L.I. et al., "The Composition of Lipids of Phytophthora-Infestans and Their Ability to Induce Potato Phytoalexin Accumulation", Database BIOSIS, Abstract No. PREV198885045135, 1987.
"MY-26-A-10 PinfestansMY Phytophthora infestans cDNA, mRNA sequence." Database EMBL, Accession No. BE777235, Sep. 21, 2000.

(Continued)

*Primary Examiner* — Elizabeth McElwain
(74) *Attorney, Agent, or Firm* — Drinker Biddle & Reath LLP

(57) ABSTRACT

The present invention relates to nucleic acid sequences coding for polypeptides with ω-3-desaturase activity. The invention furthermore relates to nucleic acid constructs, vectors and organisms comprising at least one nucleic acid sequence according to the invention, at least one vector comprising the nucleic acid sequence and/or the nucleic acid constructs, and transgenic organisms comprise the above-mentioned nucleic acid sequences, nucleic acid constructs and/or vectors.

23 Claims, 9 Drawing Sheets

(56) References Cited

FOREIGN PATENT DOCUMENTS

| | | |
|---|---|---|
| WO | WO-99/27111 | 6/1999 |
| WO | WO-99/64616 | 12/1999 |
| WO | WO-00/12720 A2 | 3/2000 |
| WO | WO-00/21557 | 4/2000 |
| WO | WO-00/34439 A1 | 6/2000 |
| WO | WO-01/59128 A2 | 8/2001 |
| WO | WO-01/85968 A2 | 11/2001 |
| WO | WO-02/08401 A2 | 1/2002 |
| WO | WO-02/26946 A2 | 4/2002 |
| WO | WO-02/44320 A2 | 6/2002 |
| WO | WO-02/057464 | 7/2002 |
| WO | WO-02/077213 A2 | 10/2002 |
| WO | WO-02/081668 A2 | 10/2002 |
| WO | WO-02/090493 A2 | 11/2002 |
| WO | WO-02/092540 A1 | 11/2002 |
| WO | WO-03/064596 | 8/2003 |
| WO | WO-03/102138 A2 | 12/2003 |
| WO | WO-2004/005442 A1 | 1/2004 |
| WO | WO-2004/057001 A2 | 7/2004 |
| WO | WO-2004/071467 | 8/2004 |
| WO | WO-2005/012316 A2 | 2/2005 |
| WO | WO-2005/083053 A2 | 9/2005 |
| WO | WO-2005/083093 A2 | 9/2005 |
| WO | WO-2005/103253 A1 | 11/2005 |
| WO | WO-2008/008099 A2 | 1/2006 |
| WO | WO-2010/057246 A2 | 5/2010 |

OTHER PUBLICATIONS

Domergue, F. et al., "Cloning and Functional Characterization of *Phaeodactylum tricornutum* Front-End Desaturases Involved in Eicosapentaenoic Acid Biosynthesis", Eur. J. Biochem. 269 (2002), pp. 4105-4113.
Horrocks, L.A. et al., "Health Benefits of Docosahexaenoic Acid (DHA)", Pharmacological Research 40:3 (1999), pp. 211-225.
Huang, Y-S. et al., "Cloning of Δ2- and Δ6-Desaturases from *Mortierella alpina* and Recombinant Production of γ-Linolenic Acid in *Saccharomyces cerevisiae*", Lipids 34:7 (1999), pp. 649-659.
Kamoun, S. et al., "Initial Assessment of Gene Diversity for the Oomycete Pathogen *Phytophthora infestans* Based on Expressed Sequences", Fungal Genetics and Biology 28 (1999), pp. 94-106.
Khozin, I. et al., "Elucidation of the Biosynthesis of Eicosapentaenoic Acid in the Microalga *Porphyridium cruentum*", Plant Physiol. 114 (1997), pp. 223-230.
McKeon, T. et al., "Stearoyl-Acyl Carrier Protein Desaturase from Safflower Seeds", in "Methods in Enzymology", vol. 71, Part C: Lipids, Editor: J. Lowenstein (1981), New York, pp. 275-281.
Pereira, S.L. et al., "A Novel ω3-Fatty Acid Desaturase Involved in the Biosynthesis of Eicosapentaenoic Acid", Biochem. J. 378 (2004), pp. 665-671.
Pereira, S.L. et al., "Recent Advances in the Study of Fatty Acid Desaturases from Animals and Lower Eukaryotes", Prostaglandins, Leukotrienes and Essential Fatty Acids 68 (2003), pp. 97-106.
Poulos, A., "Very Long Chain Fatty Acids in Higher Animals—A Review", Lipids 30:1 (1995), pp. 1-14.
Sakuradani, E. et al,, "Δ6-Fatty Acid Desaturase from an Arachidonic Acid-Producing *Mortierella* Fungus Gene Cloning and Its Heterologous Expression in a Fungus, *Aspergillus*", Gene 238 (1999), pp. 445-453.
Shimokawa, H., "Beneficial Effects of Eicosapentaenoic Acid on Endothelial Vasodilator Functions in Animals and Humans", World Rev. Nutr. Diet 88 (2001), pp. 100-108.
Spychalla, J.P. et al., "Identification of an Animal ω-3 Fatty Acid Desaturase by Heterologous Expression in *Arabidopsis*", Proc. Natl. Acad. Sci. USA 94 (1997), pp. 1142-1147.
Stukey, J.E. et al., "The OLE1 Gene of *Saccharomyces cerevisiae* Encodes the Δ9 Fatty Acid Desaturase and Can Be Functionally Replaced by the Rat Stearoyl-CoA Desaturase Gene", The Jounal of Biological Chemistry 265:33 (1990), pp. 20144-20149.

Takeyama, H. et al., "Expression of the Eicosapentaenoic Acid Synthesis Gene Cluster from *Shewanella* sp. In a Transgenic Marine Cyanobacterium, *Synechococcus* sp,", Microbiology 143 (1997), pp. 2725-2731.
Tocher, D.R. et al., "Recent Advances in the Biochemistry and Molecular Biology of Fatty Acyl Desaturases", Prog. Lipid Res. 37:2/3 (1998), pp. 73-117.
Totani, N. et al., "The Filamentous Fungus *Mortierella alpina*, High in Arachidonic Acid", Lipids, 22:2 (1987), pp. 1060-1062.
Vazhappilly, R. et al., "Heterotrophic Production Potential of Omega-3 Polyunsaturated Fatty Acids by Microalgae and Algae-like Microorganisms", Botanica Marina 41 (1998), pp. 553-558.
Wada, H. et al., "Enhancement of Chilling Tolerance of a Cyanobacterium by Genetic Manipulation of Fatty Acid Desaturation", Nature 347 (1990), pp. 200-203.
Wang X.-M. et al., "Biosynthesis and Regulation of Linolenic Acid in Higher Plants", Physiol. Biochem. 26:6 (1988), pp. 777-792.
Yu, R. et al., "Production of Eicosapentaenoic Acid by a Recombinant Marine Cyanobacterium, *Synechococcus* sp.", Lipids, 35:10 (2000), pp. 1061-1064.
Zank, T.K. et al., "Cloning and Functional Characterisation of an Enzyme Involved in the Elongation of Δ6-polyunsaturated Fatty Acids from the Moss *Physcomitrella patens*", The Plant Journal 31:3 (2002), pp. 255-268.
Chalova, L. I., et al. "The Composition of Lipids of Phytophthora infestans and Their Ability to Induce Potato Phytoalexin Accumulation", Biokhimiya, 1987, vol. 52, No. 9, pp. 1445-1453.
Broun, P., et al., "Catalytic Plasticity of Fatty Acid Modification Enzymes Underlying Chemical Diversity of Plant Lipids", Science 282:5392 (1998), pp. 1315-1317.
van de Loo, F. J., et al., "An Oleate 12-Hydroxylase from *Ricinus communis* L. is a Fatty Acyl Desaturase Homolog", Proc. Natl. Acad. Sci. U S A 92:15 (1995), pp. 6743-6747.
Doerks, T., et al., "Protein Annotation: Detective Work for Function Prediction", Trends in Genet. 14:6 (1998), pp. 248-250.
Brenner, S. E., "Errors in Genome Annotation", Trends in Genet. 15:4 (1999), pp. 132-133.
Bork, P., et al., "Go Hunting in Sequence Databases but Watch Out for the Traps", Trends in Genet. 12:10 (1996), pp. 425-427.
Millar, A.A. et al., "CUT1, an Arabidopsis Gene Required for Cuticular Wax Biosynthesis and Pollen Fertility, Encodes a Very-Long-Chain Fatty Acid Condensing Enzyme", The Plant Cell 11 (1999), pp. 825-838.
Kunau, W.-H., et al., "β-oxidation of Fatty Acids in Mitochondria, Peroxisomes, and Bacteria: A Century of Continued Progress", Prog. Lipid Res. 34:4 (1995), pp. 267-342.
Beaudoin, F. et al., "Heterologous Reconstitution in Yeast of the Polyunsaturated Fatty Acid Biosynthetic Pathway", Proceedings of the National Academy of Sciences of the United States of America 97:12 (2000), pp. 6421-6426.
Ohlrogge, J. et al., "Lipid Biosynthesis", The Plant Cell 7 (1995), pp. 957-970.
Millar, A.A. et al., "Very-long-chain Fatty Acid Biosynthesis is Controlled through the Expression and Specificity of the Condensing Enzyme", The Plant Journal 12:1 (1997), pp. 121-131.
Kajikawa, M., et al., "Isolation and Functional Characterization of Fatty Acid Δ5-Elongase Gene from the Liverwort *Marchantia polymorpha* L.", FEBS Letters, 2006, vol. 580, pp. 149-154.
Robert, S. S., et al., "Isolation and Characterisation of a Δ5-Fatty Acid Elongase from the Marine Microalga *Pavlova saline*", Mar. Biotechnol., 2009, vol. 11, pp. 410-418.
Pereira, S. L., et al., "Identification of Two Novel Microalgal Enzymes Involved in the Conversion of the ω3-Fatty Acid, Eicosapentaenoic Acid, into Docosahexaenoic Acid", Biochem. J., 2004, vol. 384, pp. 357-366.
Leonard, A. E., et al., "Elongation of Long-Chain Fatty Acids", Progress in Lipid Research, 2004, vol. 43, pp. 36-54.
Sperling, P., et al., "The Evolution of Desaturases", Prostaglandins, Leukotrienes and Essential Fatty Acids, 2003, vol. 68, pp. 73-95.
Domergue, F., et al., "New Insight into *Phaeodactylum tricornutum* Fatty Acid Metabolism. Cloning and Functional Characterization of Plastidial and Microsomal Δ12-Fatty Acid Desaturases", Plant Physiology, 2003, vol. 131, pp. 1648-1660.

(56) References Cited

OTHER PUBLICATIONS

Wu, G., et al., "Stepwise Engineering to Produce High Yields of Very Long-Chain Polyunsaturated Fatty Acids in Plants", Nature Biotechnology, 2005, vol. 23, No. 8, pp. 1013-1017.
Nakamura, M. T., et al., "Structure, Function, and Dietary Regulation of Δ6, Δ5, and Δ9 Desaturases", Annu. Rev. Nutr., 2004, vol. 24, pp. 345-376.
"P. patens Delta6 Elongase SEQ ID 29", GeneSeq Database Accession No. ABG73608, Mar. 25, 2003.
"Subname: Full = Polyunsaturated Fatty Acid Elongase elvol5a", UniProt Database Accession No. Q8AWE7, Oct. 25, 2005.
"Polyunsaturated Fatty Acid Elongase (ELOVL Family Member 5, Elongation of Long Chain Fatty Acids) (YEAST)", UniProt Database Accession No. Q8AX86, Mar. 1, 2003.
"633167 NCCCWA 1RT Oncorhynchus Mykiss cDNA Clone 1RT126D03_B_B02 5', mRNA Sequence", EMBL Database Accession No. CA360014, Nov. 7, 2002.
"LOC398440 Protein", UniProt Database Accession No. Q7ZXJ4, Jun. 1, 2003.
Huang, Y.-S., et al., "Enzymes for Transgenic Biosynthesis of Long-Chain Polyunsaturated Fatty Acids", Biochimie, 2004, vol. 86, No. 11, pp. 793-798.
"Physcomitrella patens Desaturase Encoding cDNA SEQ ID No. 7", GeneSeq Database Accession No. ABV74260, Mar. 28, 2003.
"Phaeodactylum tricornutum Desaturase Encoding cDNA SEQ ID No. 11", GeneSeq Database Accession No. ABV74262, Mar. 28, 2003.
Sprecher, H. "Metabolism of Highly Unsaturated n-3 and n-6 Fatty Acids", Biochimica et Biophysica Acta, 2000, vol. 1486, pp. 219-231.
"Nouveau Dictionnaire des Huiles Végétales: Compositions en Acides Gras", Ucciani E., Ed. Technique & Documentation—Lavoisier, 1995, ISBN: 2-7430-0009-0, pp. 577, 578 and 582.
"Phaeodactylum tricornutum Elongase Encoding cDNA SEQ ID No. 9",GeneSeq Database Accession No. ABV74261, Mar. 28, 2003.
Cronan, J. E. et al., "Biosynthesis of Membrane Lipids", in *E. coli und Salmonella*, Section B2, Neidhart, F.C. et al. eds., ASM Press, Washington, DC, (1996), pp. 612-636.
Gerhardt, B., "Fatty Acid Degradation in Plants", Prog. Lipid Res. 31:4 (1992), pp. 417-446.
Magnuson, K. et al., "Regulation of Fatty Acid Biosynthesis in *Escherichia coli*", Microbiological Reviews, 57:3 (1993), pp. 522-542.
Stymne, S., "Biosynthesis of 'Uncommon' Fatty Acids and Their Incorporation into Triacylglycerols", Biochemistry and Molecular Biology of Membrane and Storage Lipids of Plants, N. Murata et al., Editors, The American Society of Plant Physiologists (1993), pp. 150-158.
Frentzen, M., "Acyltransferases from Basic Science to Modified Seed Oils", Fett/Lipid, 100:4-5, S. (1998), pp. 166-166.
Shanklin, J. et al., "Desaturation and Related Modifications of Fatty Acids", Annu. Rev. Plant Physiol. Plant Mol. Biol. 49 (1998), pp. 611-641.
Drexler, H. et al., "Metabolic Engineering of Fatty Acids for Breeding of New Oilseed Crops: Strategies, Problems and First Results", J. Plant Physiol. 160 (2003), pp. 779-802.
Tvrdik, P. et al., "Role of a New Mammalian Gene Family in the Biosynthesis of Very Long Chain Fatty Acids and Sphingolipids", The Journal of Cell Biology, 149:3 (2000) pp. 707-717.
Guehnemann-Schaefer, K. et al., "Fatty Acid β-oxidation in Glyoxysomes. Characterization of a New Tetrafunctional Protein (MFPIII)", Biochimica et Biophysica Acta 1256 (1995), pp. 181-186.
Meyer, A. et al., "Novel Fatty Acid Elongases and Their Use for the Reconstitution of Docosahexaenoic Acid Biosynthesis", Journal of Lipid Research 45 (2004), pp. 1899-1909.
Kinney, A.J., "Genetic Engeering of Oilseeds for Desired Traits", in "Genetic Engineering, Principles and Methods", vol. 19 (1997), Editor: J. Setlow, pp. 149-166.

Voelker, T., "Plant Acyl-ACP Thioesterases: Chain-Length Determining Enzymes in Plant Fatty Acid Biosynthesis", in "Genetic Engineering, Principles and Methods", vol. 18 (1996), Editor: J. Setlow, pp. 111-113.
Zank, T.K. et al., "Cloning and Functional Expression of the First Plant Fatty Acid Elongase Speicific for $\Delta^6$-Polyunsaturated Fatty Acids", Biochemical Society Trasactions 28:6 (2000), pp. 654-658.
Murphy, D.J. et al., "Biosynthesis, Targetting and Processing of Oleosin-like Proteins, Which are Major Pollen Coat Components in *Brassica napus*", The Plant Journal 13:1 (1998), pp. 1-16.
Domergue. F., et al., "Acyl Carriers Used as Substrates by the Desaturases and Elongases Involved in Very Long-chain Polyunsaturated Fatty Acids Biosynthesis Reconstituted in Yeast", The Journal of Biological Chemistry, 2003, vol. 278, No. 37, pp. 35115-35126.
Gunstone, F. D., "Vegetable Oils", In: Bailey's Industrial Oil and Fat Products, Sixth Edition, Six Volume Set, pp. 213-267, Ed. Shahidi, John Wiley & Sons, Inc., 2005.
Ursin, V., et al., "Production of Beneficial Dietary Omega-3 and Omega 6 Fatty Acids in Transgenic Canola", Abstract No. 49, 14th International Symposium Plant Lipids, 2000.
U.S. Appl. No. 60/613,861 Singh et al.
Wolff, R. L., et al., "Arachidonic, Eicosapentaenoic, and Biosynthetically Related Fatty Acids in the Seed Lipids from a Primitive Gymnosperm, *Agathis robusta* ", Lipids, 1999, vol. 34, No. 10, pp. 1083-1097.
Hong, H., et al., "High-Level Production of γ-Linolenic Acid in *Brassica juncea* Using a Δ6 Desaturase from *Pythium irregular* ", Plant Physiology, 2002, vol. 129, pp. 354-362.
Abbadi, A., et al., "Transgenic Oilseeds as Sustainable Source of Nutritionally Relevant C20 and C22 Polyunsaturated Fatty Acids?", Eur. J. Lipid Sci. Technol., 2001, vol. 103, pp. 106-113.
Sayanova, O. V., et al., "Eicosapentaenoic Acid: Biosynthetic Routes and the Potential for Synthesis in Transgenic Plants", Phytochemistry, 2004, vol. 65, pp. 147-158.
Heinz, E., "Docosahexaenoic Acid (DHA) in Transgenic Oilseeds: Which Approach Will Be Successful First?", European Journal of Lipid Science and Technology, 2002, vol. 104, pp. 1-2.
Lui, J.-W., et al., "Evaluation of the Seed Oils from a Canola Plant Genetically Transformed to Produce High Levels of γ-Linolenic Acid", Chapter 7 in "γ-Linolenic acid: Recent Advances in Biotechnology and Clinical Applications", Eds. Huang and Ziboh, AOCS Press, Champaign, Illinois, 2001, pp. 61-71.
Derelle, E., et al., "DNA Libraries for Sequencing the Genome of *Ostreococcus tauri* (Chlorophyta, Prasinophyceae): The Smallest Free-Living Eukaryotic Cell", J. Phycol, 2002, vol. 38, pp. 1150-1156.
Derelle, E., et al., "Genome Analysis of the Smallest Free-Living Eukaryote *Ostreococcus tauri* Unveils Many Unique Features", PNAS, 2006, vol. 103, No. 31, pp. 11647-11652.
Ral, J.-P., et al., "Starch Division and Partitioning. A Mechanism for Granule Propagation and Maintenance in the Picophytoplanktonic Green Alga *Ostreococcus tauri* ", Plant Physiology, 2004, col. 136, pp. 3333-3340.
"*Ostreococcus tauri* Delta-6-Desaturase (d6) Gene, Complete cds", Database EMBL Accession No. AY746357, Jul. 8, 2005.
Sayanova, O. V., et al., "Identification of *Primula* Fatty Acid $\Delta^5$Desaturases with n-3 Substrate Preferences", FEBS Letters, 2003, vol. 542, pp. 100-104.
Beaudoin, F., et al., "Production of $C_{20}$ Polysaturated Fatty Acids (PUFAs) by Pathway Engineering: Identification of a PUFA Elongase Component from *Caenorhabditis elegans*", Biochemical Society Transactions, 2000, vol. 28, pp. 661-663.
Parker-Barnes, J. M., et al., "Identification and Characterization of an Enzyme Involved in the Elongation of n-6 and n-3 Polyunsaturated Fatty Acids", PNAS, vol. 97, 2000, vol. 97, No. 15, pp. 8284-8289.
Thurmond, T. Das J. M. et al., "Polyunsaturated Fatty Acid-Specific Elongation Enzymes", Biochemical Society Transactions, 2000, vol. 28, pp. 658-660.
Sato, S., et al., "Production of γ-Linolenic Acid and Stearidonic Acid in Seeds of Marker-Free Transgenic Soybean", Crop Science, 2004, vol. 28, pp. 658-660.

(56) References Cited

OTHER PUBLICATIONS

Inagaki, K., "Identification and Expression of a Rat Acid Elongase Involved in the Biosynthesis of C18 Fatty Acids", Biosci. Biotechnol. Biochem., 2002, vol. 66, No. 3, pp. 613-621.

Wallis, J. G. et al., "The $\gamma^6$-Desaturase of *Euglena gracillis*: An Alternate Pathway for Synthesis of 20-Carbon Polyunsaturated Fatty Acids", Archives of Biochemistry and Biophysics, 1999, vol. 365, No. 2, pp. 307-316.

Qi, B., et al., "Identification of a cDNA Encoding a Novel C18-$\gamma^9$ Polyunsaturated Fatty Acid-Specific Elongating Activity From the Docosahexaenoic Acid (DHA)-Producting Microalga, *Isochrysis Galbana*", FEBS Letters, 2002, vol. 510, pp. 159-165.

Qi. B., et al., "Production of Very Long Chain Polyunsaturated Omega-3 and Omega-6 Fatty Acids In Plants", Nature Biotechnology, 2004, vol. 22, No. 6, pp. 739-745.

Knutzon, D. S., et al., "Identification of Δ5-Desaturase from *Morierella alpina* by Heterologous Expression in Bakers' Yeast and Canola", The Journal of Biological Chemistry, 1998, vol. 273, No. 45, pp. 29360-29366.

Leonard, A. E., et al., "cDNA Cloning and Characterization of Human Δ5 Desaturase involved in the Biosynthesis of Arachidonic Acid", Biochem. J., 2000, vol. 347, pp. 719-724.

Hong, H., et al., "Isolation and Characterization of a Δ5 FA Desaturase from *Pythium Irregulare* by Heterologous Expression in *Seccharomyces cerevisiae* and Oilseed Crops", Lipids, 2002, vol. 37, No. 9, pp. 863-868.

Leonard, A. E., et al., "Cloning of a human cDNA Encoding a Novel Enzyme Involved in the Elongation of a Long-Chain Polyunsaturated Fatty Acids", Biochem. J., 2000, vol. 350, pp. 765-770.

Leonard, A. E., et al., "Identification and Expression of Mammalian Long-Chain PUFA Elongation Enzymes", Lipids, 2002, vol. 37, No. 8, pp. 733-740.

Agaba, M., et al., "Zebrafish cDNA Encoding Multifunctional Fatty Acid Elongase Involved in Production of Eicosapentaenoic (20:5n-3) and Docosahexaenoic (22:6n-3) Acids", Marine Biotechnology, 2004, vol. 6, pp. 251-261.

Armbrust, E. V., et al., "The Genome of the Diatom *Thalassiosira pseudonana*: Ecology, Evolution, and Metabolism", Science, 2004, vol. 306, pp. 79-86.

Clough, S. J., et al., "Floral Dip: A Simplified Method for Agrobacterium-Mediated Transformation of *Arabidopsis thaliana*", The Plant Journal, 1998, vol. 16, No. 6, pp. 735-743.

Qiu, X., et al., "Identification of a Δ4 Fatty Acid Desaturase from *Thraustochytrium* sp. Involved in the Biosynthesis of Docosahexanoic Acid by Heterologous Expression in *Saccharomyces cerevisiae* and *Brassica juncea*", The Journal of Biological Chemistry, 2001, vol. 276, No. 34, pp. 31561-31566.

Millar, A. A., et al., "Accumulation of Very-Long-Chain Fatty Acids in Membrane Glycerolipids Is Associated with Dramatic Alterations in Plant Morphology", The Plant Cell, 1998, vol. 11, pp. 1889-1902.

Robert, S. S., et al., "Metabolic Engineering of *Arabidopsis* to Produce Nutritionally Important DHA in Seed Oil", Functional Plant Biology, 2005, vol. 32, pp. 473-479.

Domergue, F., et al., "In Vivo Characterization of the First Acyl-CoA Δ$^6$ -Desaturase from a Member of the Plant Kingdom, the Microalga *Ostreococcus tauri*", Biochem. J., 2005, vol. 389, pp. 483-490.

Venegas-Calerón, M., et al., "An Alternative to Fish Oils: Metabolic Engineering of Oil-Seed Crops to Produce Omega-3 Long Chain Polyunsaturated Fatty Acids", Progress in Lipid Research, 2010, vol. 49, pp. 108-119.

Meyer, A., et al., "Biosynthesis of Docosahexaenoic Acid in *Euglena gracillis*: Biochemical and Molecular Evidence for the Involvement of a Δ4-Fatty Acyl Group Desaturase", Biochemistry, 2003, vol. 42, pp. 9779-9788.

\* cited by examiner

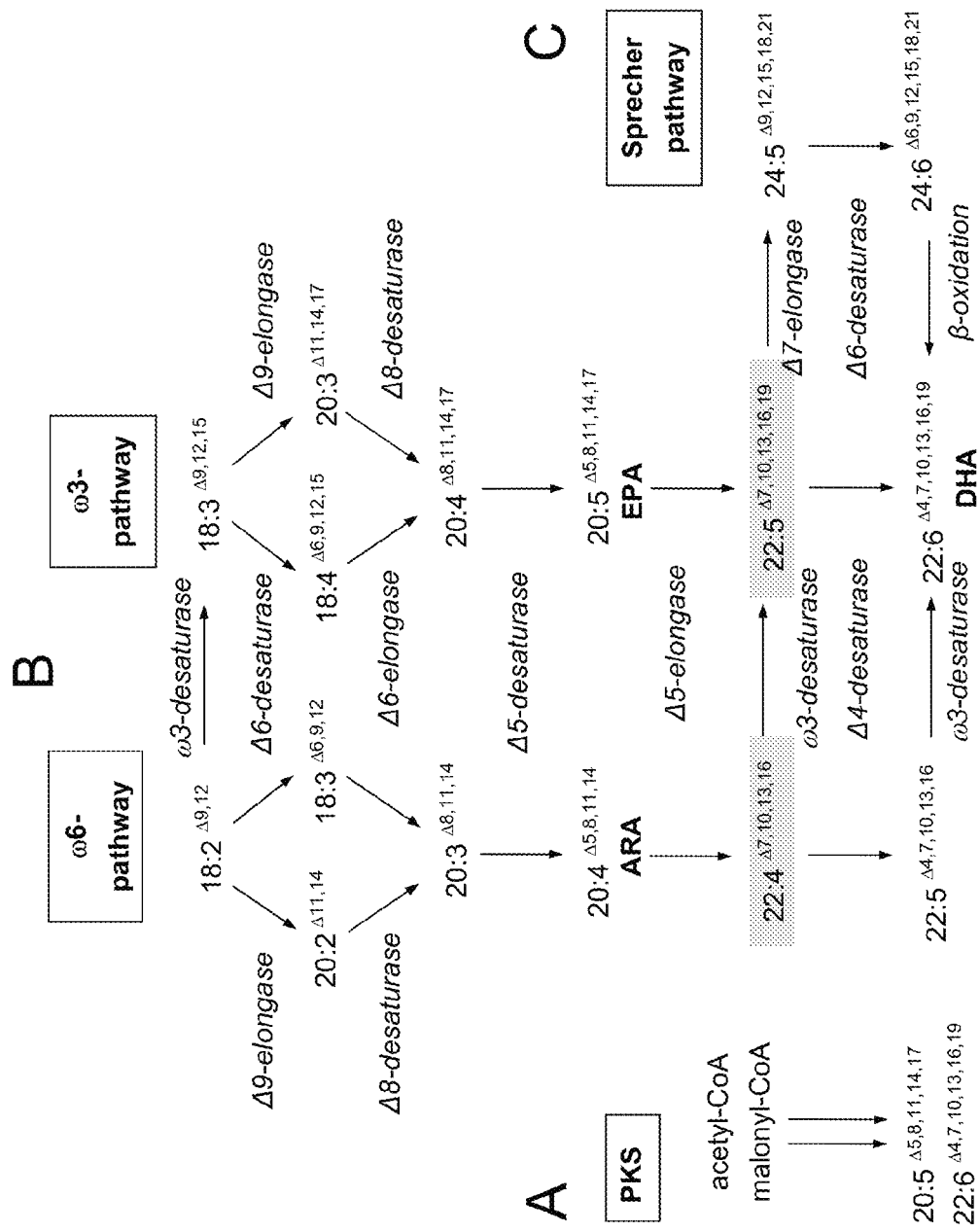
Figure 1: Various synthetic pathways for the biosynthesis of DHA (docosahexaenoic acid)

Figure 2: Desaturation of linoleic acid (18:2 ω6-fatty acid) to α-linolenic acid (18:3 ω3-fatty acid) by Pi-omega3Des.
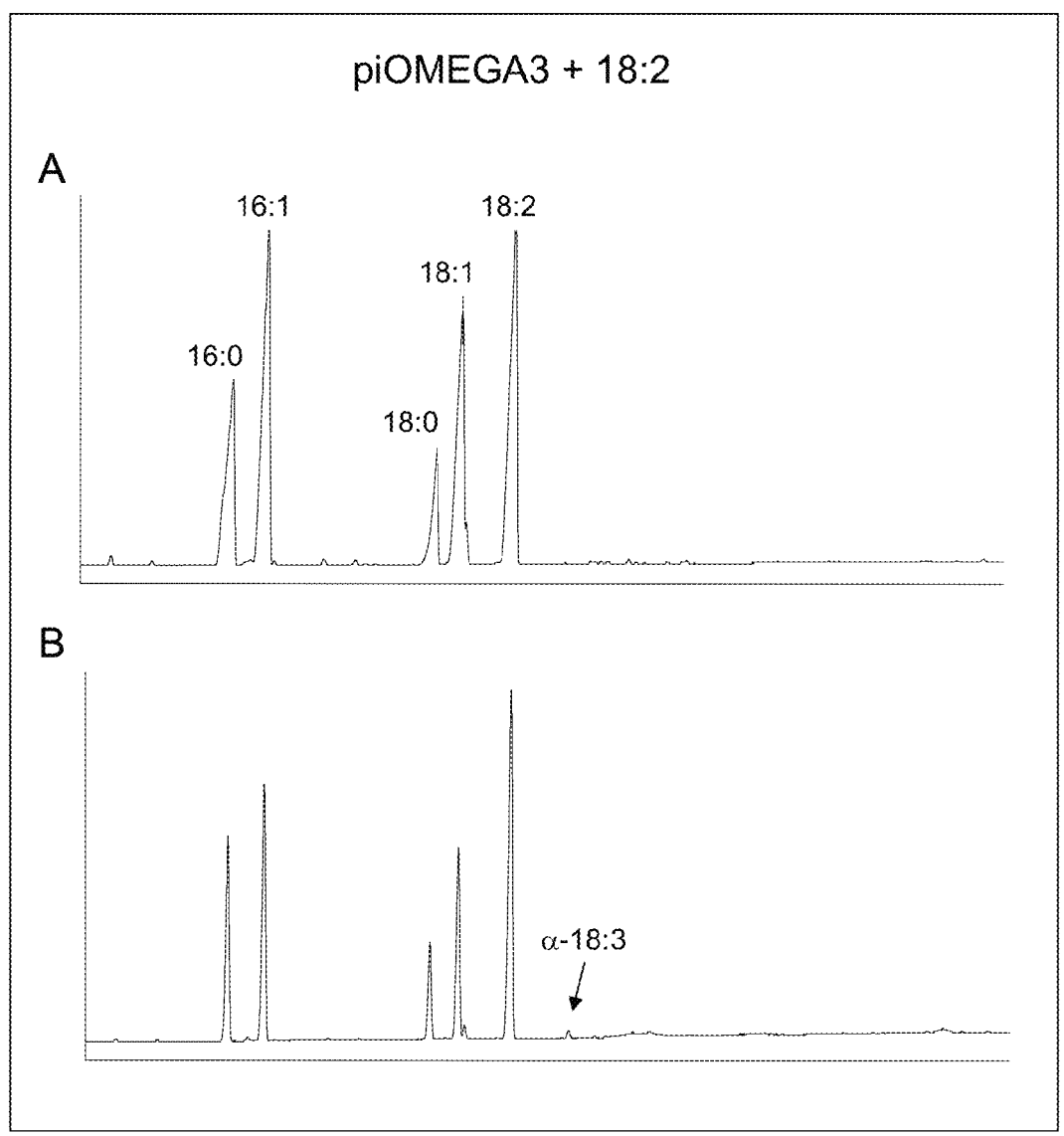

Figure 3: Desaturation of γ-linolenic acid (18:3 ω6-fatty acid) to stearidonic acid (18:4 ω3-fatty acid) by Pi-omega3Des.
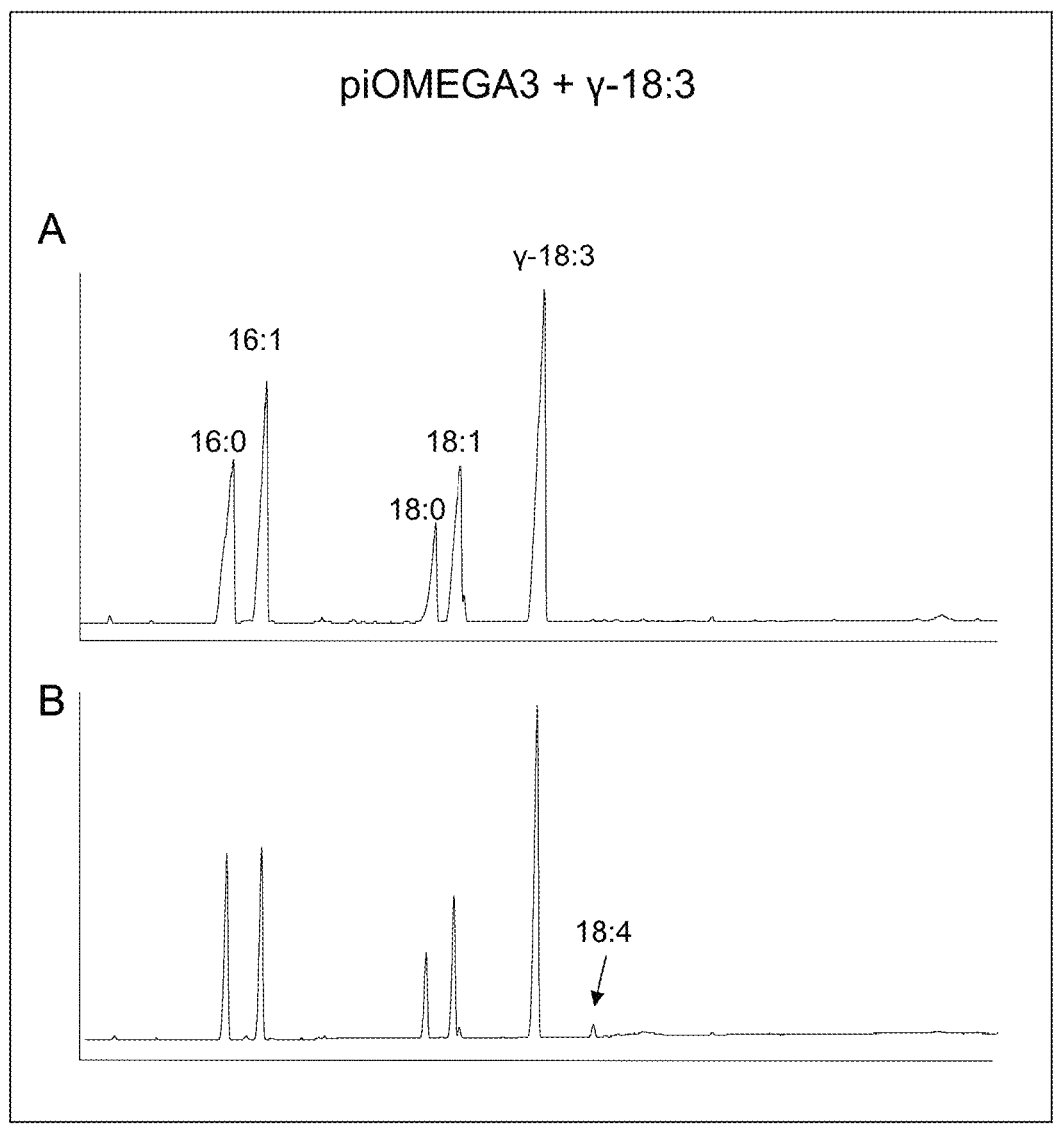

Figure 4: Desaturation of C20:2 ω6-fatty acid to C20:3 ω3-fatty acid by Pi-omega3Des.
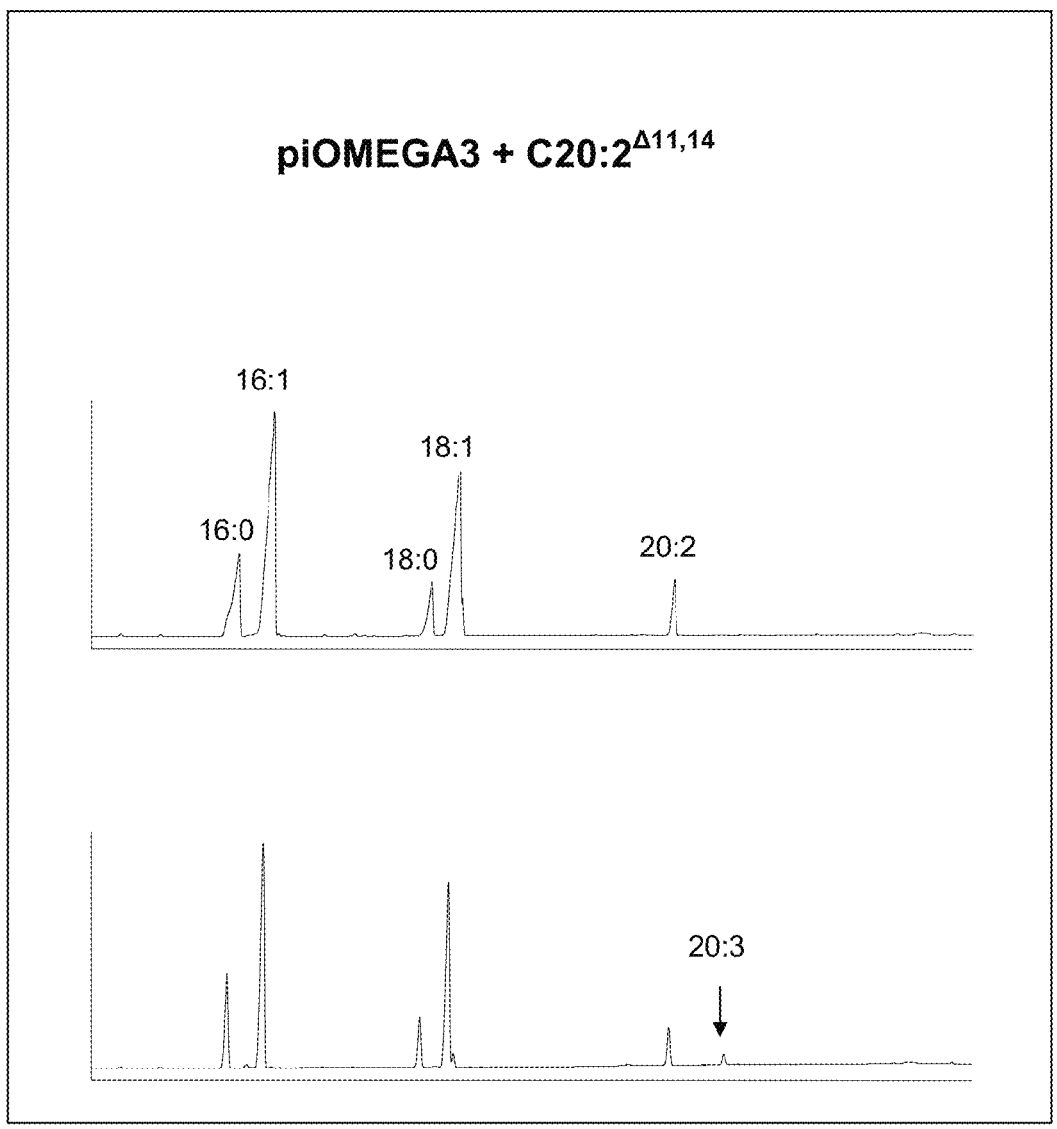

Figure 5: Desaturation of C20:3 ω6-fatty acid to C20:4 ω3-fatty acid by Pi-omega3Des.
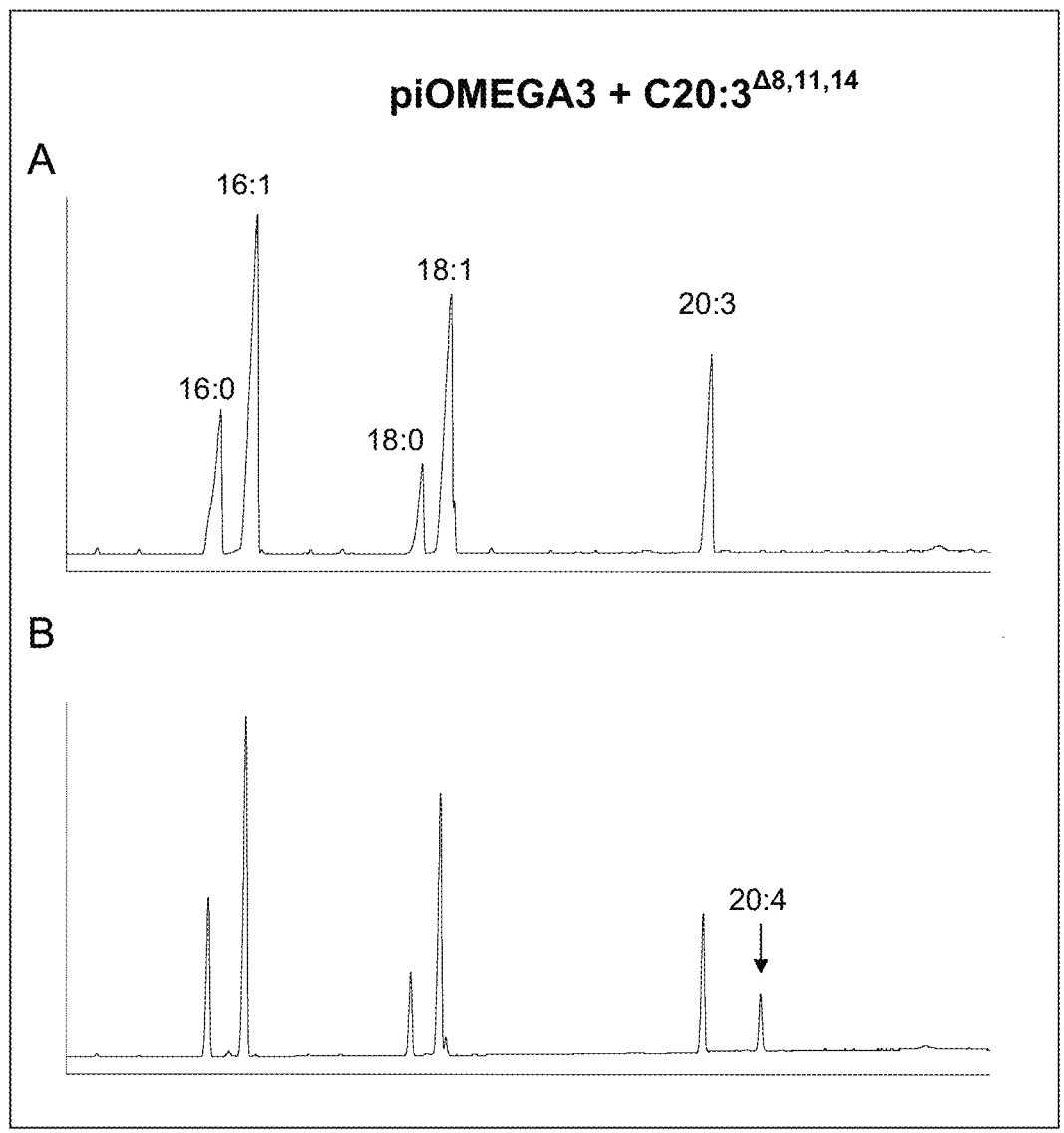

Figure 6: Desaturation of arachidonic acid (C20:4 ω6-fatty acid) to eicosapentaenoic acid (C20:5 ω3-fatty acid) by Pi-omega3Des.
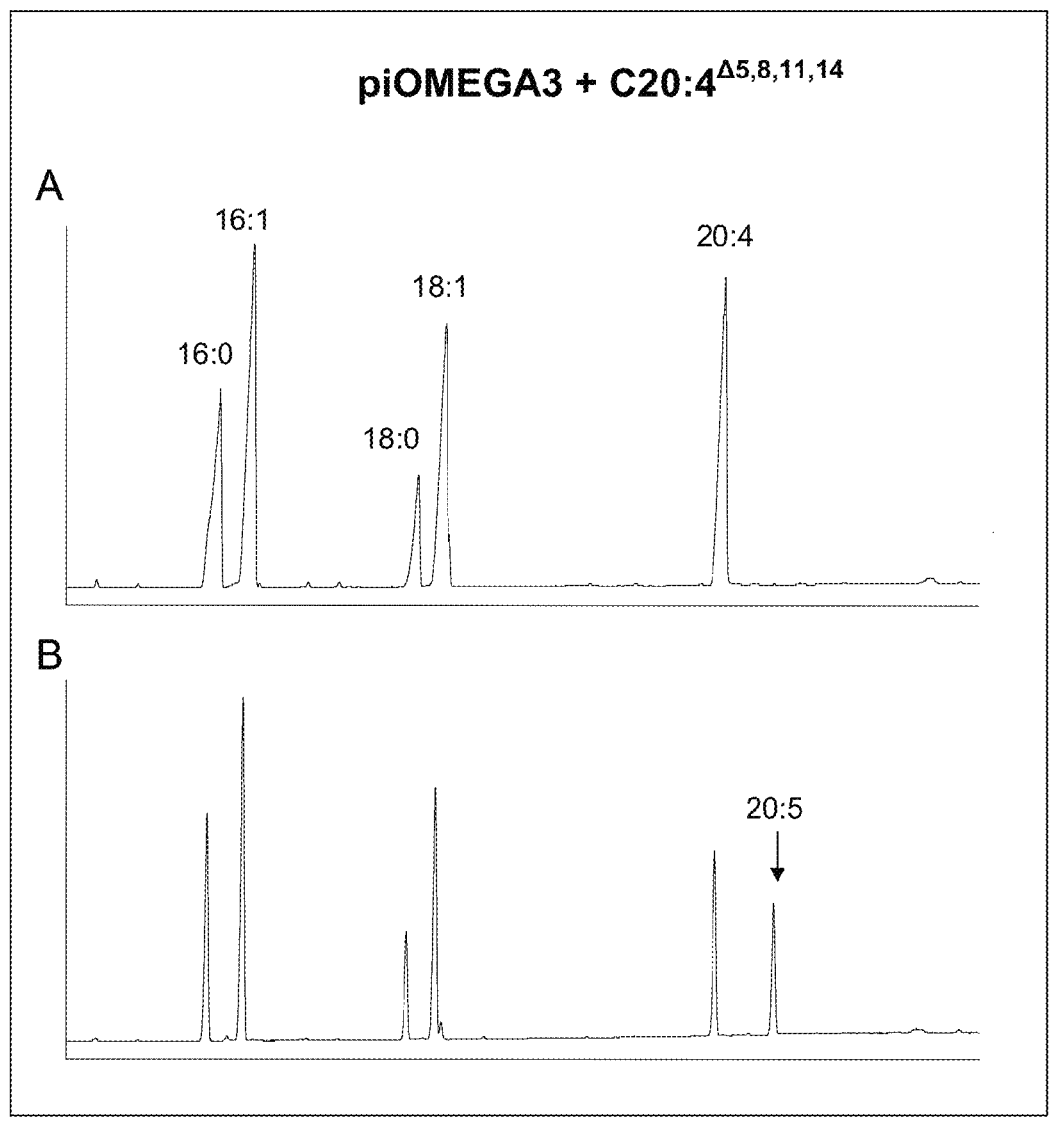

Figure 7: Desaturation of docosatetraenoic acid (C22:4 ω6-fatty acid) to docosapentaenoic acid (C22:5 ω3-fatty acid) by Pi-omega3Des.
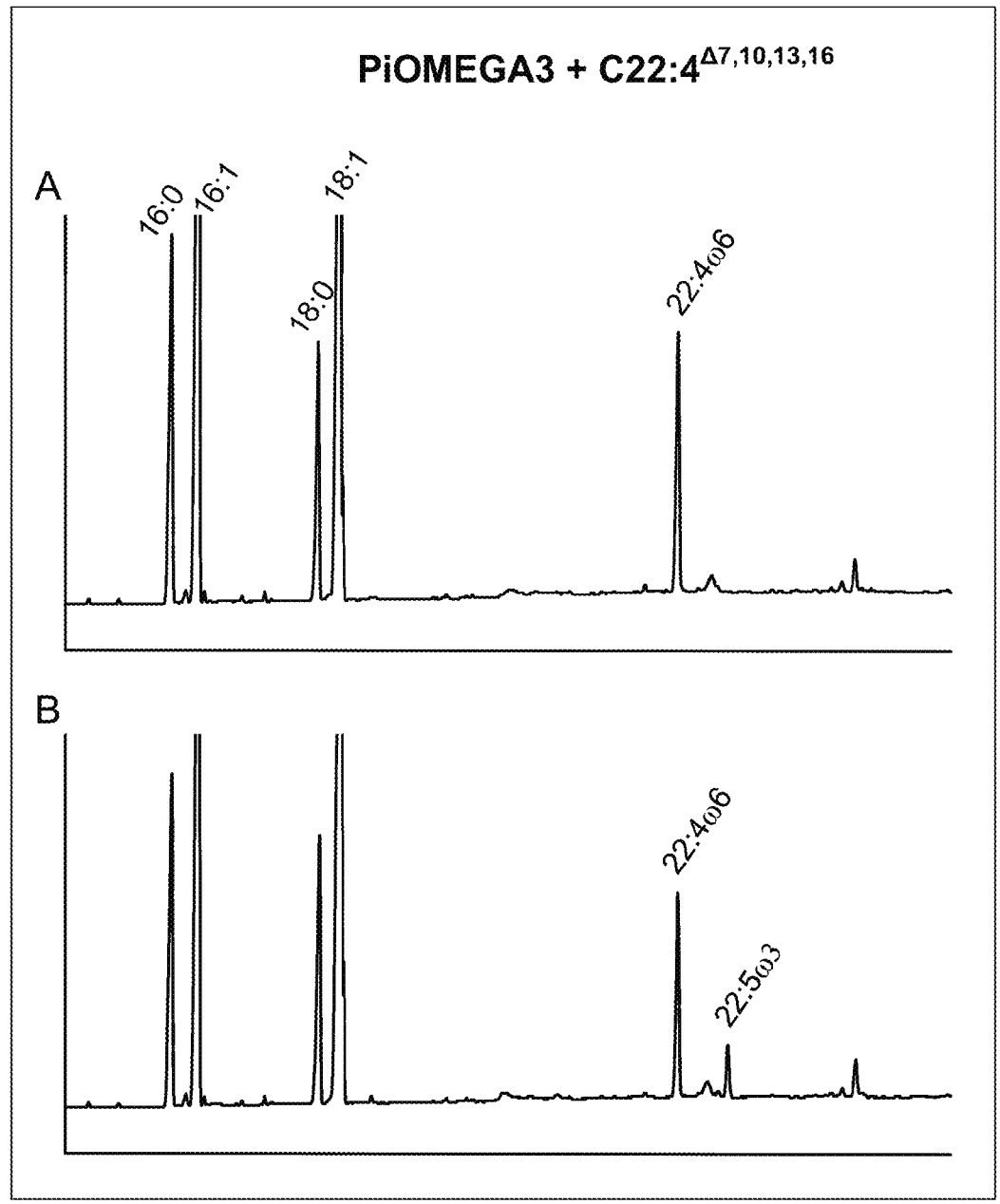

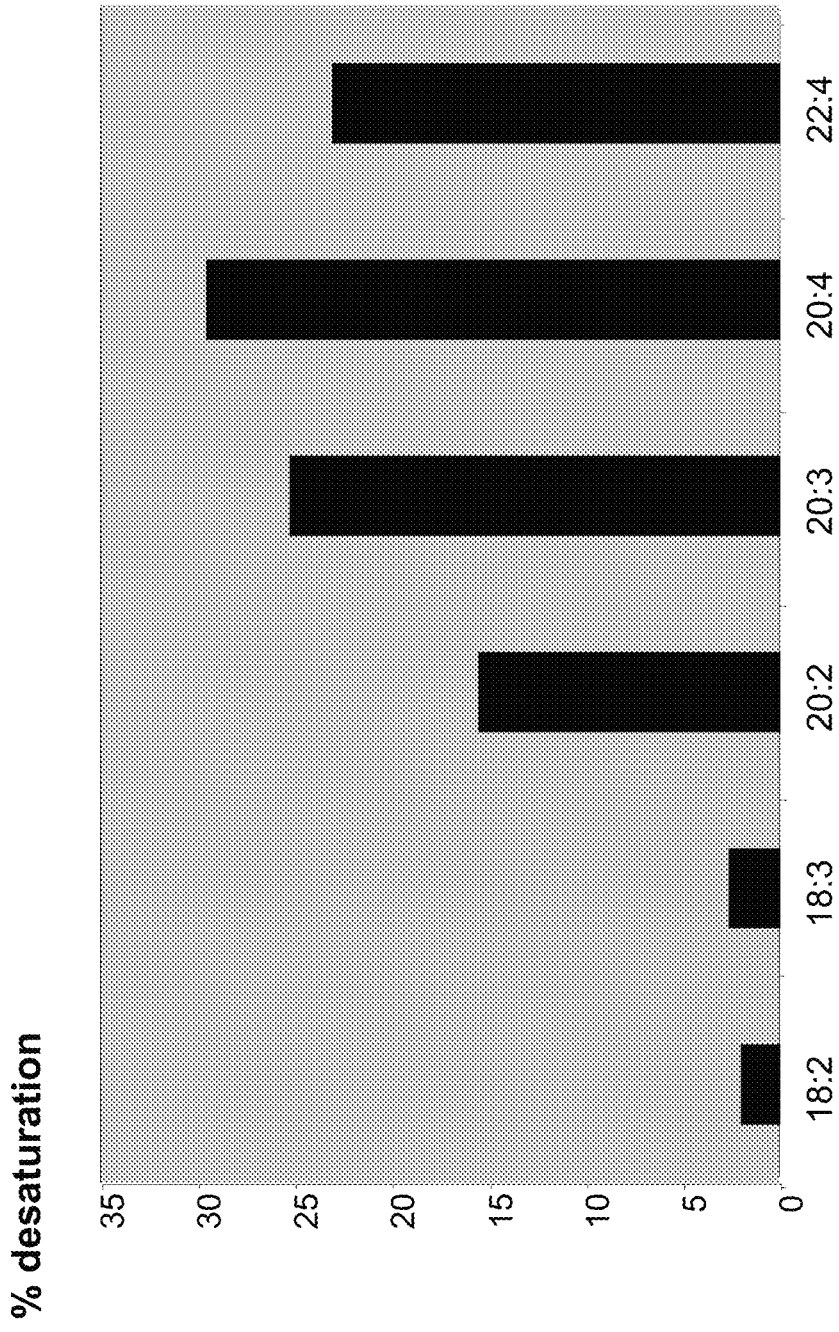
Figure 8: Substrate specificity of Pi-omega3Des with regard to a variety of fatty acids

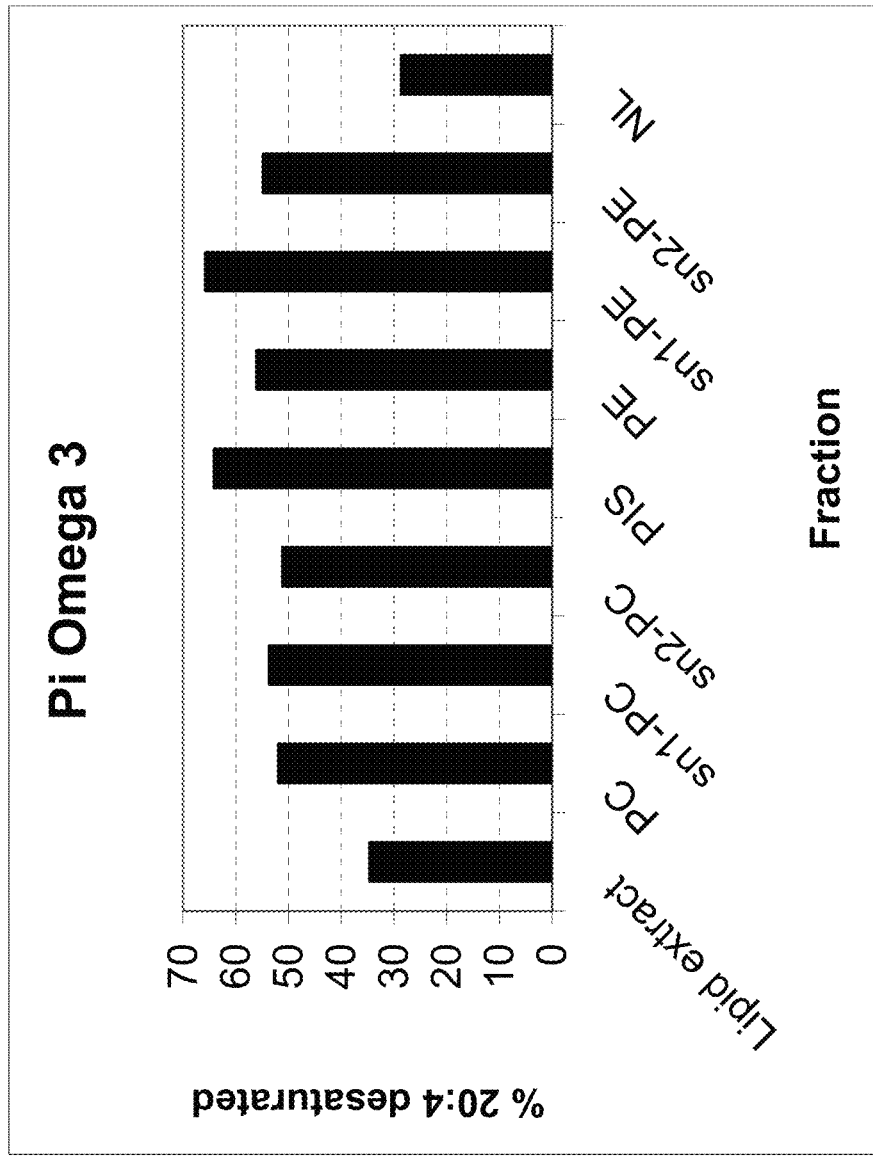
Figure 9: Desaturation of phospholipid-bound arachidonic acid to EPA by Pi-Omega3Des

SEQUENCE LISTING

```
<160> NUMBER OF SEQ ID NOS: 6

<210> SEQ ID NO 1
<211> LENGTH: 1086
<212> TYPE: DNA
<213> ORGANISM: Phytophthora infestans
<220> FEATURE:
<221> NAME/KEY: CDS
<222> LOCATION: (1)..(1086)
<223> OTHER INFORMATION: Omega-3-desaturase

<400> SEQUENCE: 1 atg gcg acg aag gag gcg tat gtg ttc ccc act ctg acg gag atc aag      48
Met Ala Thr Lys Glu Ala Tyr Val Phe Pro Thr Leu Thr Glu Ile Lys
1               5                   10                  15 cgg tcg cta cct aaa gac tgt ttc gag gct tcg gtg cct ctg tcg ctc      96
Arg Ser Leu Pro Lys Asp Cys Phe Glu Ala Ser Val Pro Leu Ser Leu
            20                  25                  30 tac tac acc gtg cgt tgt ctg gtg atc gcg gtg gct cta acc ttc ggt     144
Tyr Tyr Thr Val Arg Cys Leu Val Ile Ala Val Ala Leu Thr Phe Gly
        35                  40                  45 ctc aac tac gct cgc gct ctg ccc gag gtc gag agc ttc tgg gct ctg     192
Leu Asn Tyr Ala Arg Ala Leu Pro Glu Val Glu Ser Phe Trp Ala Leu
    50                  55                  60 gac gcc gca ctc tgc acg ggc tac atc ttg ctg cag ggc atc gtg ttc     240
Asp Ala Ala Leu Cys Thr Gly Tyr Ile Leu Leu Gln Gly Ile Val Phe
65                  70                  75                  80 tgg ggc ttc ttc acg gtg ggc cac gat gcc ggc cac ggc gcc ttc tcg     288
Trp Gly Phe Phe Thr Val Gly His Asp Ala Gly His Gly Ala Phe Ser
                85                  90                  95
```

```
cgc tac cac ctg ctt aac ttc gtg gtg ggc act ttc atg cac tcg ctc      336
Arg Tyr His Leu Leu Asn Phe Val Val Gly Thr Phe Met His Ser Leu
            100                 105                 110 atc ctc acg ccc ttc gag tcg tgg aag ctc acg cac cgt cac cac cac      384
Ile Leu Thr Pro Phe Glu Ser Trp Lys Leu Thr His Arg His His His
        115                 120                 125 aag aac acg ggc aac att gac cgt gac gag gtc ttc tac ccg caa cgc      432
Lys Asn Thr Gly Asn Ile Asp Arg Asp Glu Val Phe Tyr Pro Gln Arg
    130                 135                 140 aag gcc gac gac cac ccg ctg tct cgc aac ctg att ctg gcg ctc ggg      480
Lys Ala Asp Asp His Pro Leu Ser Arg Asn Leu Ile Leu Ala Leu Gly
145                 150                 155                 160 gca gcg tgg ctc gcc tat ttg gtc gag ggc ttc cct cct cgt aag gtc      528
Ala Ala Trp Leu Ala Tyr Leu Val Glu Gly Phe Pro Pro Arg Lys Val
                165                 170                 175 aac cac ttc aac ccg ttc gag cct ctg ttc gtg cgt cag gtg tca gct      576
Asn His Phe Asn Pro Phe Glu Pro Leu Phe Val Arg Gln Val Ser Ala
            180                 185                 190 gtg gta atc tct ctt ctc gcc cac ttc ttc gtg gcc gga ctc tcc atc      624
Val Val Ile Ser Leu Leu Ala His Phe Phe Val Ala Gly Leu Ser Ile
        195                 200                 205 tat ctg agc ctc cag ctg ggc ctt aag acg atg gca atc tac tac tat      672
Tyr Leu Ser Leu Gln Leu Gly Leu Lys Thr Met Ala Ile Tyr Tyr Tyr
    210                 215                 220 gga cct gtt ttt gtg ttc ggc agc atg ctg gtc att acc acc ttc cta      720
Gly Pro Val Phe Val Phe Gly Ser Met Leu Val Ile Thr Thr Phe Leu
225                 230                 235                 240 cac cac aat gat gag gag acc cca tgg tac gcc gac tcg gag tgg acg      768
His His Asn Asp Glu Glu Thr Pro Trp Tyr Ala Asp Ser Glu Trp Thr
                245                 250                 255 tac gtc aag ggc aac ctc tcg tcc gtg gac cga tcg tac ggc gcg ctc      816
Tyr Val Lys Gly Asn Leu Ser Ser Val Asp Arg Ser Tyr Gly Ala Leu
            260                 265                 270 att gac aac ctg agc cac aac atc ggc acg cac cag atc cac cac ctt      864
Ile Asp Asn Leu Ser His Asn Ile Gly Thr His Gln Ile His His Leu
    275                 280                 285 ttc cct atc att ccg cac tac aaa ctc aag aaa gcc act gcg gcc ttc      912
Phe Pro Ile Ile Pro His Tyr Lys Leu Lys Lys Ala Thr Ala Ala Phe
290                 295                 300 cac cag gct ttc cct gag ctc gtg cgc aag agc gac gag cca att atc      960
His Gln Ala Phe Pro Glu Leu Val Arg Lys Ser Asp Glu Pro Ile Ile
305                 310                 315                 320 aag gct ttc ttc cgg gtt gga cgt ctc tac gca aac tac ggc gtt gtg     1008
Lys Ala Phe Phe Arg Val Gly Arg Leu Tyr Ala Asn Tyr Gly Val Val
                325                 330                 335 gac cag gag gcg aag ctc ttc acg cta aag gaa gcc aag gcg gcg acc     1056
Asp Gln Glu Ala Lys Leu Phe Thr Leu Lys Glu Ala Lys Ala Ala Thr
            340                 345                 350 gag gcg gcg gcc aag acc aag tcc acg taa                             1086
Glu Ala Ala Ala Lys Thr Lys Ser Thr
    355                 360

<210> SEQ ID NO 2
<211> LENGTH: 361
<212> TYPE: PRT
<213> ORGANISM: Phytophthora infestans

<400> SEQUENCE: 2

Met Ala Thr Lys Glu Ala Tyr Val Phe Pro Thr Leu Thr Glu Ile Lys
1               5                   10                  15
```

```
Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
 50                  55                  60

Asp Ala Ala Leu Cys Thr Gly Tyr Ile Leu Leu Gln Gly Ile Val Phe
 65                  70                  75                  80

Trp Gly Phe Phe Thr Val Gly His Asp Ala Gly His Gly Ala Phe Ser
                 85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
            115                 120                 125

Lys Asn Thr Gly Asn Ile Asp Arg Asp Glu Val Phe Tyr Pro Gln Arg
130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
            195                 200                 205

Tyr Leu Ser Leu Gln Leu Gly Leu Lys Thr Met Ala Ile Tyr Tyr Tyr
 210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
            275                 280                 285

Phe Pro Ile Ile Pro His Tyr Lys Leu Lys Lys Ala Thr Ala Ala Phe
 290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
            355                 360

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
taagcttaca tggcgacgaa ggagg                                        25
```

```
<210> SEQ ID NO 4
<211> LENGTH: 24
<212> TYPE: DNA
<213> ORGANISM: Artificial sequence
<220> FEATURE:
<223> OTHER INFORMATION: Primer

<400> SEQUENCE: 4
tggatccact tacgtggact tggt                                              24

<210> SEQ ID NO 5
<211> LENGTH: 24
<212> TYPE: DNA
<213> ORGANISM: Artificial sequence
<220> FEATURE:
<223> OTHER INFORMATION: Primer

<400> SEQUENCE: 5
ctggttcagg tgcattcgcc ggcg                                              24

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
gcggccgcat ggcgacgaag gagg                                              24
```

METHOD FOR PRODUCING UNSATURATED OMEGA-3-FATTY ACIDS IN TRANSGENIC ORGANISMS

RELATED APPLICATIONS

This application is a divisional of U.S. application Ser. No. 12/768,227, filed Apr. 27, 2010, which is a divisional of U.S. application Ser. No. 10/590,958, filed Aug. 25, 2006, now U.S. Pat. No. 7,777,098, which is the national stage application (under 35 U.S.C. 371) of PCT/EP2005/001865 filed Feb. 23, 2005, which claims benefit of German application 10 2004 009 458.6 filed Feb. 27, 2004. The entire contents of each of these applications are hereby incorporated by reference herein.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13987_00217. The size of the text file is 10 KB, and the text file was created on Jan. 9, 2013.

FIELD OF THE INVENTION

The present invention relates to a process for production of unsaturated ω-3-fatty acids and to a process for production of triglycerides with an elevated content of unsaturated fatty acids, especially of ω-3-fatty acids having more than three double bonds. The invention relates to the production of a transgenic organism, preferably of a transgenic plant or of a transgenic microorganism, with an elevated content of unsaturated ω-3-fatty acids, oils or lipids having ω-3-double bonds as the result of the expression of an ω-3-desaturase from fungi of the family Pythiaceae such as the genus *Phytophtora*, for example of the genus and species *Phytophtora infestans*.

The invention furthermore relates to the nucleic acid sequences, nucleic acid constructs, vectors and organisms comprising at least one nucleic acid sequence according to the invention, at least one vector comprising the nucleic acid sequence and/or the nucleic acid constructs, and transgenic organisms comprise the abovementioned nucleic acid sequences, nucleic acid constructs and/or vectors.

A further part of the invention relates to oils, lipids and/or fatty acids produced by the process according to the invention, and to their use. The invention moreover relates to unsaturated fatty acids and triglycerides with an elevated content of unsaturated fatty acids and their use.

DESCRIPTION OF RELATED ART

Fatty acids and triacylglycerides have a multiplicity of applications in the food industry, in animal nutrition, in cosmetics and the pharmacological sector. Depending on whether they are free saturated or unsaturated fatty acids or else triacylglycerides with an elevated content of saturated or unsaturated fatty acids, they are suitable for very different applications.

Polyunsaturated long-chain ω-3-fatty acids such as eicosapentaenoic acid (=EPA, C20:5$^{\Delta5,8,11,14,17}$) or docosahexaenoic acid (=DHA, C22:6$^{\Delta4,7,10,13,16,19}$) are important components of human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). There is therefore a demand for the production of polyunsaturated long-chain fatty acids.

Owing to the present-day composition of human food, an addition of polyunsaturated ω-3-fatty acids, which are preferentially found in fish oils, to the food is particularly important. Thus, for example, polyunsaturated fatty acids such as DHA or EPA are added to infant formula to improve the nutritional value. The unsaturated fatty acid DHA is supposed to have a positive effect on the development and maintenance of brain functions.

In the text which follows, polyunsaturated fatty acids are referred to as PUFA, PUFAs, LCPUFA or LCPUFAs (poly unsaturated fatty acids, PUFA, long chain poly unsaturated fatty acids, LCPUFA).

The various fatty acids and triglycerides are mainly obtained from microorganisms such as *Mortierella* or *Schizochytrium* or from oil-producing plants such as soybeans, oilseed rape, algae such as *Crypthecodinium* or *Phaeodactylum* and others, being obtained, as a rule, in the form of their triacylglycerides (=triglycerides=triglycerols). However, they can also be obtained from animals, for example, fish. The free fatty acids are advantageously prepared by hydrolysis. Very long-chain polyunsaturated fatty acids such as DHA, EPA, arachidonic acid (=ARA, C20: 4$^{\Delta5,8,11,14}$), dihomo-γ-linolenic acid (C20:3$^{\Delta8,11,14}$) or docosapentaenoic acid (DPA, C22:5$^{\Delta7,10,13,16,19}$) are not synthesized in plants, for example in oil crops such as oilseed rape, soybeans, sunflowers and safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω-3-fatty acids are said to have a positive effect on the cholesterol level in the blood and thus on the possibility of preventing heart disease. The risk of heart disease, stroke or hypertension can be reduced markedly by adding these ω-3-fatty acids to the food. Also, ω-3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω-6-fatty acids such as arachidonic acid tend to have an adverse effect on these disorders in connection with these rheumatic diseases on account of our usual dietary intake.

ω-3- and ω-6-fatty acids are precursors of tissue hormones, known as eicosanoids, such as the prostaglandins, which are derived from dihomo-γ-linolenic acid, arachidonic acid and eicosapentaenoic acid, and of the thromoxanes and leukotrienes, which are derived from arachidonic acid and eicosapentaenoic acid. Eicosanoids (known as the PG$_2$ series) which are formed from the ω-6-fatty acids generally promote inflammatory reactions, while eicosanoids (known as the PG$_3$ series) from ω-3-fatty acids have little or no proinflammatory effect. Therefore food having a high proportion of ω-3-fatty acid has a positive effect on human health.

Owing to their positive characteristics, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. Nos. 5,614,393, 5,614,393 WO 96/21022, WO 00/21557 and WO 99/27111, and also the application for the production in transgenic organisms is described in WO 98/46763, WO 98/46764 and WO 98/46765. Here, the expression of various desaturases is also described and claimed in WO 99/64616 or WO 98/46776, as is the formation of polyunsaturated fatty acids. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Furthermore, mixtures of ω-3- and ω-6-fatty acids are usually obtained.

Especially suitable microorganisms for the production of PUFAs are microorganisms such as microalgae such as *Phaeodactylum tricornutum, Porphiridium* species, *Thraustochytrium* species, *Schizochytrium* species or *Cryptheco-dinium* species, ciliates such as *Stylonychia* or *Colpidium*, fungi such as *Mortierella, Entomophthora* or *Mucor* and/or mosses such as *Physcomitrella, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process, which is why as described above recombinant methods are preferred wherever possible. However, only limited amounts of the desired polyunsaturated fatty acids such as DPA, EPA or ARA can be produced with the aid of the abovementioned microorganisms; where they are generally obtained as fatty acid mixtures of, for example, EPA, DPA and ARA, depending on the microorganism used.

A variety of synthetic pathways is being discussed for the synthesis of the polyunsaturated fatty acids arachidonic acid, eicosapentaenoic acid and docosahexaenoic acid (FIG. 1). Thus, EPA or DHA are produced in numerous marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1197)).

An alternative strategy is the alternating activity of desaturases and elongases (Zank, T. K. et al. Plant Journal 31:255-268, 2002; Sakuradani, E. et al. Gene 238:445-453, 1999). A modification of the above-described pathway by Δ6-desaturase, Δ6-elongase, Δ5-desaturase, Δ5-elongase and Δ4-desaturase is the Sprecher pathway (Sprecher 2000, Biochim. Biophys. Acta 1486:219-231) in mammals. Instead of the Δ4-desaturation, a further elongation step is effected here to give $C_{24}$, followed by a further Δ6-desaturation and finally β-oxidation to give the $C_{22}$ chain length. What is known as the Sprecher pathway (see FIG. 1) is, however, not suitable for the production in plants and microorganisms since the regulatory mechanisms are not known.

Depending on their desaturation pattern, the polyunsaturated fatty acids can be divided into two large classes, viz. ω-6- or ω-3-fatty acids, which differ with regard to their metabolic and functional activities (FIG. 1).

The starting material for the ω-6-metabolic pathway is the fatty acid linoleic acid ($18:2^{\Delta9,12}$) while the ω-3-pathway proceeds via linolenic acid ($18:3^{\Delta9,12,15}$). Linolenic acid is formed by the activity of an ω-3-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and ω-3-desaturase) and must take up these fatty acids (essential fatty acids) via the food. Starting with these precursors, the physiologically important polyunsaturated fatty acids arachidonic acid (=ARA, $20:4^{\Delta5,8,11,14}$), an ω-6-fatty acid and the two ω-3-fatty acids eicosapentaenoic acid (=EPA, $20:5^{\Delta5,8,11,14,17}$) and docosa-hexaenoic acid (DHA, $22:6^{\Delta4,7,10,13,17,19}$) are synthesized via the sequence of desaturase and elongase reactions. The application of ω-3-fatty acids shows the therapeutic activity described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

From the angle of nutritional physiology, it is therefore important to achieve a shift between the ω-6-synthetic pathway and the ω-3-synthetic pathway (see FIG. 1) in the synthesis of polyunsaturated fatty acids so that more ω-3-fatty acids are produced. The enzymatic activities of various ω-3-desaturases which desaturate $C_{18:2}$-, $C_{22:4}$- or $C_{22:5}$-fatty acids have been described in the literature (see FIG. 1). However, none of the desaturases whose biochemistry has been described converts a broad range of substrates of the ω-6-synthetic pathway into the corresponding fatty acids of the ω-3-synthetic pathway.

There is therefore still a great demand for an ω-3-desaturase which is suitable for the production of ω-3-polyunsaturated fatty acids. All the known plant and cyanobacterial ω-3-desaturases desaturate C18-fatty acids with linoleic acid as the substrate, but cannot desaturate C20- or C22-fatty acids.

An ω-3-desaturase which can desaturate C20-polyunsaturated fatty acids is known from the fungus *Saprolegnia dicilina* (Pereira et al. 2003, Biochem. J. 2003 Dez, manuscript BJ20031319). However, it is disadvantageous that this ω-3-desaturase cannot desaturate C18- or C22-PUFAs, such as the important fatty acids C18:2-, C22:4- or C22:5-fatty acids of the ω-6-synthetic pathway. A further disadvantage of this enzyme is that it cannot desaturate fatty acids which are bound to phospholipids. Only the CoA-fatty acid esters are converted.

To make possible the fortification of food and/or of feed with these polyunsaturated ω-3-fatty acids, there is therefore a great need for a simple, inexpensive process for the production of these polyunsaturated fatty acids, especially in eukaryotic systems.

BRIEF SUMMARY OF THE INVENTION

The object of the invention was therefore to provide further genes or enzymes which are suitable for the synthesis of LCPUFAs and which allow a shift from the ω-6-synthetic pathway to the ω-3-synthetic pathway, specifically genes which have an ω-3-desaturase activity, for the production of polyunsaturated fatty acids.

BRIEF DESCRIPTION OF THE DRAWINGS

FIG. 1 shows various synthetic pathways for the biosynthesis of DHA (docosahexaenoic acid).

FIG. 2 shows desaturation of linoleic acid (18:2 ω6-fatty acid) to α-linolenic acid (18:3 ω3-fatty acid) by Pi-omega3Des.

FIG. 3 shows desaturation of γ-linolenic acid (18:3 ω6-fatty acid) to stearidonic acid (18:4 ω3-fatty acid) by Pi-omega3Des.

FIG. 4 shows desaturation of C20:2 ω6-fatty acid to C20:3 ω3-fatty acid by Pi-omega3Des.

FIG. 5 shows desaturation of C20:3 ω6-fatty acid to C20:4 ω3-fatty acid by Pi-omega3Des.

FIG. 6 shows desaturation of arachidonic acid (C20:4 ω6-fatty acid) to eicosapentaenoic acid (C20:5 ω3-fatty acid) by Pi-omega3Des.

FIG. 7 shows desaturation of docosatetraenoic acid (C22:4 ω6-fatty acid) to docosapentaenoic acid (C22:5 ω3-fatty acid) by Pi-omega3Des.

FIG. 8 shows substrate specificity of Pi-omega3Des with regard to a variety of fatty acids.

FIG. 9 shows desaturation of phospholipid-bound arachidonic acid to EPA by Pi-Omega3Des.

DETAILED DESCRIPTION OF THE INVENTION

The object of the invention was furthermore to develop a process for the production of polyunsaturated ω-3-fatty acids in an organism, advantageously in a eukaryotic organism, preferably a plant or a microorganism. This object was achieved by the process according to the invention for the production of compounds of the general formula I

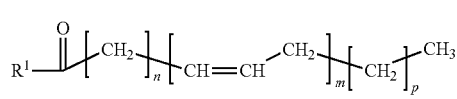

(I)

in transgenic organisms with a content of at least 1% by weight of these compounds based on the total lipid content of the transgenic organism, which comprises the following process steps:
a) introducing, into the organism, at least one nucleic acid sequence which encodes an ω-3-desaturase activity, and
b) culturing the organism under conditions which permits the production of compounds of the general formula I, and where the variables and substituents in formula I have the following meanings:
$R^1$=hydroxyl, coenzyme A (thioester), lysophosphatidylcholine, lysophosphatidylethanolamine, lysophosphatidyl-glycerol, lyso-diphosphatidylglycerol, lysophosphatidylserine, lysophosphatidylinositol, sphingo base or a radical of the formula II

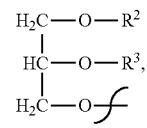

(II)

$R^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, $R^3$=hydrogen, saturated or unsaturated $C_2$-$C_{24}$-alkylcarbonyl, or $R^2$ and $R^3$ independently of one another are a radical of the formula Ia:

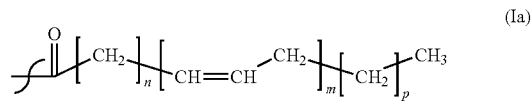

(Ia)

n=2, 3, 4, 5, 6, 7 or 9, m=2, 3, 4, 5 or 6 and p=0 or 3.

$R^1$ in the general formula I is hydroxyl, coenzyme A (thioester), lysophosphatidylcholine, lysophosphatidylethanolamine, lysophosphatidylglycerol, lyso-diphosphatidylglycerol, lysophosphatidylserine, lysophosphatidylinositol, sphingo base or a radical of the formula II

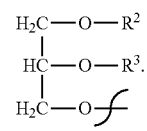

(II)

The abovementioned radicals of $R^1$ are always bonded to the compounds of the general formula I in the form of their thioesters.

$R^2$ in the general formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 18, 20 or 22 carbon atoms in the fatty acid chain comprise up to six double bonds, advantageously two, three, four or five double bonds, especially preferably two, three or four double bonds. All the abovementioned radicals are derived from the corresponding fatty acids.

$R^3$ in the formula II is hydrogen, saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl-, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 18, 20 or 22 carbon atoms in the fatty acid chain comprise up to six double bonds, advantageously two, three, four or five double bonds, especially preferably two, three or four double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The polyunsaturated fatty acids produced in the process according to the invention advantageously comprise at least two, advantageously three, four, five or six, double bonds. The fatty acids especially advantageously comprise two, three, four or five double bonds. Fatty acids produced in the process advantageously have 18, 20 or 22 C atoms in the fatty acid chain; the fatty acids preferably comprise 20 or 22 carbon atoms in the fatty acid chain. Saturated fatty acids are advantageously reacted to a minor degree, or not at all, by the nucleic acids used in the process. To a minor degree is to be understood as meaning that the saturated fatty acids are reacted with less than 5% of the activity, advantageously less than 3%, especially advantageously with less than 2% of the activity in comparison with polyunsaturated fatty acids. These fatty acids which have been produced can be produced in the process as a single product or be present in a fatty acid mixture.

The nucleic acid sequences used in the process according to the invention take the form of isolated nucleic acid sequences which encode polypeptides with ω-3-desaturase activity.

Nucleic acid sequences which are advantageously used in the process according to the invention are nucleic acid sequences which encode polypeptides with ω-3-desaturase activity selected from the group consisting of:
a) a nucleic acid sequence with the sequence shown in SEQ ID NO: 1, or
b) nucleic acid sequences which, as the result of the degeneracy of the genetic code, can be derived from the amino acid sequences shown in SEQ ID NO: 2, or
c) derivatives of the nucleic acid sequence shown in SEQ ID NO: 1, which encode polypeptides with at least 60% identity at the amino acid level with SEQ ID NO: 2, and which have an ω-3-desaturase activity.

Advantageously, the substituents $R^2$ or $R^3$ in the general formulae I and II independently of one another are saturated or unsaturated $C_{18}$-$C_{22}$-alkylcarbonyl; especially advantageously, are independently of one another unsaturated $C_{18}$-, $C_{20}$- or $C_{22}$-alkylcarbonyl with at least two double bonds.

The polyunsaturated fatty acids produced in the process are advantageously bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms; preferred are the long-chain fatty acids, especially preferred are the long-chain fatty acids LCPUFAs of $C_{18}$-, $C_{20}$- and/or $C_{22}$-fatty acids.

The process according to the invention advantageously yields fatty acid esters with polyunsaturated $C_{18}$-, $C_{20}$- and/or $C_{22}$-fatty acid molecules with at least two double bonds in the fatty acid ester, advantageously with at least two, three, four, five or six double bonds in the fatty acid ester, especially advantageously of at least three, four, five or six double bonds in the fatty acid ester, advantageously leading to the synthesis of linolenic acid (=LA, C18:2$^{\Delta 9,12,15}$), γ-linolenic acid (=GLA, C18:3$^{\Delta 6 9,12}$), stearidonic acid (=SDA, C18:4$^{\Delta 6,9,12,15}$), dihomo-γ-linolenic acid (=DGLA, 20:3$^{\Delta 8,11,14}$), ω-3-eicosatetraenoic acid (=ETA, C20:4$^{\Delta 8,11,14,17}$), arachidonic acid (ARA, C20:4$^{\Delta 5,8,11,14}$), eicosapentaenoic acid (EPA, C20:5$^{\Delta 5,8,11,14,17}$), ω-6-docosapentaenoic acid ($C_{22:5}^{\Delta 4,7,10,13,16}$), ω-3-docosapentaenoic acid ($C_{22:5}^{\Delta 7,10,13,16,19}$), docosahexaenoic acid (=DHA, C22:6$^{\Delta 4,7,10,13,16,19}$) or their mixtures, preferably ARA, EPA and/or DHA.

The fatty acid esters with polyunsaturated $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters which comprise the polyunsaturated fatty acids with at least two, three, four, five or six, preferably five or six, double bonds, from the organisms which were used for the preparation of the fatty acid esters; preferably, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, preferably in the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

In the process according to the invention, the LCPUFAs which have been produced are produced in a content of at least 3% by weight, advantageously at least 5% by weight, preferably at least 8% by weight, especially preferably at least 10% by weight, very especially preferably at least 15% by weight, based on the total fatty acids in the transgenic organisms, advantageously in a transgenic plant. The fatty acids are advantageously produced in bound form. It is possible, with the aid of the nucleic acids used in the process according to the invention, for these unsaturated fatty acids to be positioned at the sn1, sn2 and/or sn3 position of the triglycerides which have advantageously been produced. In the PUFA production process, the ω-3-desaturase sequences according to the invention are advantageously used in combination with further genes of the PUFA synthesis, such as the Δ4-desaturase, Δ5-desaturase, Δ6-desaturase, Δ8-desaturase, Δ5-elongase, Δ6-elongase and/or Δ9-elongase gene. This is how, in the process according to the invention, the end products of the process, for example arachidonic acid (ARA), eicosapentaenoic acid (EPA), ω-6-docosapentaenoic acid or DHA are produced from the starting compounds linoleic acid (C18:2) or linolenic acid (C18:3) via a number of reaction steps. As a rule, these are not generated as absolutely pure products, small traces of the precursors being, as a rule, also present in the end product. If, for example, both linoleic acid and linolenic acid are present in the starting organism, or the starting plant, the end products, such as ARA, EPA or DHA, are present as mixtures. The precursors should advantageously not amount to more than 20% by weight, preferably not to more than 15% by weight, especially preferably not to more than 10% by weight, very especially preferably not to more than 5% by weight, based on the amount of the end product in question. Advantageously, only ARA, EPA or only DHA, bound or as free acids, are produced as end products in the process of the invention in a transgenic plant. If the compounds ARA, EPA and DHA are produced simultaneously, they are advantageously produced in a ratio of at least 1:1:2 (EPA:ARA:DHA), advantageously at least 1:1:3, preferably 1:1:4, especially preferably 1:1:5.

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Arachidonic acid as advantageous polyunsaturated fatty acid is present in the fatty acid esters or fatty acid mixtures in a concentration of preferably at least 0.1; 0.2; 0.3; 0.4; 0.5; 0.6; 0.7; 0.8; 0.9 or 1%, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (β-hydroxy-9c,11t-octadecadienoic acid). The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, $C22:5^{\Delta4,8,12,15,21}$) and no nisinic acid (tetracosahexaenoic acid, $C_{23:6}^{\Delta3,8,12,15,18,21}$).

Owing to the nucleic acid sequences according to the invention or nucleic acid sequences used in the process according to the invention, an increase in the yield of polyunsaturated ω-3-fatty acids of at least 50%, advantageously at least 80%, especially advantageously at least 100%, very especially advantageously at least 150% in comparison with the nontransgenic starting organism, for example a yeast, an alga, a fungus or a plant such as *Arabidopsis* or flax when compared by means of GC analysis; see Examples.

Chemically pure polyunsaturated fatty acids or fatty acid compositions can also be synthesized by the processes described above. To this end, the fatty acids or the fatty acid compositions are isolated from the organism such as the microorganisms or the plants or the culture medium in which or on which the organisms have been cultured, or from the organism and the culture medium in the known manner, for example via extraction, distillation, crystallization, chromatography or a combination of these methods. These chemically pure fatty acids or fatty acid compositions are advantageous for applications in the food industry sector, the cosmetic sector and especially the pharmacological industry sector.

A suitable organism for the production in the process according to the invention is, in principle, any organism such as microorganisms, nonhuman animals or plants.

Plants which are suitable are, in principle, all those plants which are capable of synthesizing fatty acids, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as Tagetes.

Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopo-diaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [manihot] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium* flexifolium, Physcomitrium hookeri, Physcomitrium hookeri var. serratum, Physcomitrium immersum, Physcomitrium kellermanii, Physcomitrium megalocarpum, Physcomitrium pyriforme, Physcomitrium pyriforme var. serratum, Physcomitrium rufipes, Physcomitrium sandbergii, Physcomitrium subsphaericum, Physcomitrium washingtoniense, Geraniaceae, such as the genera Pelargonium, Cocos, Oleum, for example the genera and species Cocos nucifera, Pelargonium grossularioides or Oleum cocois [coconut], Gramineae, such as the genus Saccharum, for example the genus and species Saccharum officinarum, Juglandaceae, such as the genera Juglans, Wallia, for example the genera and species Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra or Wallia nigra [walnut], Lauraceae, such as the genera Persea, Laurus, for example the genera and species Laurus nobilis [bay], Persea americana, Persea gratissima or Persea persea [avocado], Leguminosae, such as the genus Arachis, for example the genus and species Arachis hypogaea [peanut], Linaceae, such as the genera Linum, Adenolinum, for example the genera and species Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne var. lewisii, Linum pratense or Linum trigynum [linseed], Lythrarieae, such as the genus Punica, for example the genus and species Punica granatum [pomegranate], Malvaceae, such as the genus Gossypium, for example the genera and species Gossypium hirsutum, Gossypium arboreum, Gossypium barbadense, Gossypium herbaceum or Gossypium thurberi [cotton], Marchantiaceae, such as the genus Marchantia, for example the genera and species Marchantia berteroana, Marchantia foliacea, Marchantia macropora, Musaceae, such as the genus Musa, for example the genera and species Musa nana, Musa acuminata, Musa paradisiaca, Musa spp. [banana], Onagraceae, such as the genera Camissonia, Oenothera, for example the genera and species Oenothera biennis or Camissonia brevipes [evening primrose], Palmae, such as the genus Elacis, for example the genus and species Elaeis guineensis [oil palm], Papaveraceae, such as the genus Papaver, for example the genera and species Papaver orientale, Papaver rhoeas, Papaver dubium [poppy], Pedaliaceae, such as the genus Sesamum, for example the genus and species Sesamum indicum [sesame], Piperaceae, such as the genera Piper, Artanthe, Peperomia, Steffensia, for example the genera and species Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata [cayenne pepper], Poaceae, such as the genera Hordeum, Secale, Avena, Sorghum, Andropogon, Holcus, Panicum, Oryza, Zea (maize), Triticum, for example the genera and species Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum [barley], Secale cereale [rye], Avena sativa, Avena fatua, Avena byzantina, Avena fatua var. sativa, Avena hybrida [oats], Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum [millet], Oryza sativa, Oryza latifolia [rice], Zea mays [maize], Triticum aestivum, Triticum durum, Triticum turgidum, Triticum hybernum, Triticum macha, Triticum sativum or Triticum vulgare [wheat], Porphyridiaceae, such as the genera Chroothece, Flintiella, Petrovanella, Porphyridium, Rhodella, Rhodosorus, Vanhoeffenia, for example the genus and species Porphyridium cruentum, Proteaceae, such as the genus Macadamia, for example the genus and species Macadamia intergrifolia [macadamia], Prasinophyceae such as the genera Nephroselmis, Prasinococcus, Scherffelia, Tetraselmis, Mantoniella, Ostreococcus, for example the genera and species Nephroselmis olivacea, Prasinococcus capsulatus, Scherffelia dubia, Tetraselmis chui, Tetraselmis suecica, Mantoniella squamata, Ostreococcus tauri, Rubiaceae such as the genus Cofea, for example the genera and species Cofea spp., Coffea arabica, Coffea canephora or Coffea liberica [coffee], Scrophulariaceae such as the genus Verbascum, for example the genera and species Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum or Verbascum thapsus [mullein], Solanaceae such as the genera Capsicum, Nicotiana, Solanum, Lycopersicon, for example the genera and species Capsicum annuum, Capsicum annuum var. glabriusculum, Capsicum frutescens [pepper], Capsicum annuum [paprika], Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris [tobacco], Solanum tuberosum [potato], Solanum melongena [eggplant], Lycopersicon esculentum, Lycopersicon lycopersicum, Lycopersicon pyriforme, Solanum integrifolium or Solanum lycopersicum [tomato], Sterculiaceae, such as the genus Theobroma, for example the genus and species Theobroma cacao [cacao] or Theaceae, such as the genus Camellia, for example the genus and species Camellia sinensis [tea].

Advantageous microorganisms are, for example, fungi selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Sacharomycetaceae, Saprolegniaceae, Schizosacharomycetaceae, Sodariaceae or Tuberculariaceae.

Examples which may be mentioned are the following microorganisms selected from the group: Choanephoraceae such as the genera Blakeslea, Choanephora, for example the genera and species Blakeslea trispora, Choanephora cucurbitarum, Choanephora infundibulifera var. cucurbitarum, Mortierellaceae, such as the genus Mortierella, for example the genera and species Mortierella isabellina, Mortierella polycephala, Mortierella ramanniana, Mortierella vinacea, Mortierella zonata, Pythiaceae such as the genera Phytium, Phytophthora for example the genera and species Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae var. parasitica, Phytophthora palmivora, Phytophthora parasitica, Phytophthora syringae, Saccharomycetaceae such as the genera Hansenula, Pichia, Saccharomyces, Saccharomycodes, Yarrowia for example the genera and species Hansenula anomala, Hansenula californica, Hansenula canadensis, Hansenula capsulata, Hansenula ciferrii, Hansenula glucozyma, Hansenula henricii, Hansenula holstii, Hansenula minuta, Hansenula nonfermentans, Hansenula philodendri, Hansenula polymorpha, Hansenula saturnus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilliermondii, Pichia haplophila, Pichia henricii, Pichia holstii, Pichia jadinii, Pichia lindnerii, Pichia membranaefaciens, Pichia methanolica, Pichia minuta var. minuta, Pichia minuta var. nonfermentans, Pichia norvegensis, Pichia ohmeri, Pichia pastoris, Pichia philodendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceti, Saccharomyces bailii, Saccharomyces bayanus, Saccharomyces bisporus, Saccharomyces capensis, Saccharomyces carlsbergensis, Saccharomyces cerevisiae, Saccharomyces cerevisiae var. ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii, Yarrowia lipolytica, Schizosacharomycetaceae such as the genera Schizosaccharomyces e.g. the species Schizosaccharomyces japonicus var. japonicus, Schizosaccharomyces japonicus var. versatilis, Schizosaccharomyces malidevorans, Schizosaccharomyces octosporus, Schizosaccharomyces pombe var. malidevorans, Schizosaccharomyces pombe var. pombe, Thraustochytriaceae such as the genera Althornia, Aplanochytrium, Japonochytrium, Schizochytrium, Thraustochytrium e.g. the species Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum or Thraustochytrium visurgense.

Further advantageous microorganisms are, for example, bacteria selected from the group of the families Bacillaceae, Enterobacteriacae or Rhizobiaceae.

Examples which may be mentioned are the following microorganisms selected from the group: Bacillaceae such as the genera Bacillus for example the genera and species Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus subsp. fusiformis, Bacillus galactophilus, Bacillus globisporus, Bacillus globisporus subsp. marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis subsp. spizizenii, Bacillus subtilis subsp. subtilis or Bacillus thuringiensis; Enterobacteriacae such as the genera Citrobacter, Edwardsiella, Enterobacter, Erwinia, Escherichia, Klebsiella, Salmonella or Serratia for example the genera and species Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter sp., Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora subsp. atroseptica, Erwinia carotovora subsp. betavasculorum, Erwinia carotovora subsp. odorifera, Erwinia carotovora subsp. wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli var. communior, Escherichia colimutabile, Escherichia fergusonii, Escherichia hermannii, Escherichia sp., Escherichia vulneris, Klebsiella aerogenes, Klebsiella edwardsii subsp. atlantae, Klebsiella ornithinolytica, Klebsiella oxytoca, Klebsiella planticola, Klebsiella pneumoniae, Klebsiella pneumoniae subsp. pneumoniae, Klebsiella sp., Klebsiella terrigena, Klebsiella trevisanii, Salmonella abony, Salmonella arizonae, Salmonella bongori, Salmonella choleraesuis subsp. arizonae, Salmonella choleraesuis subsp. bongori, Salmonella choleraesuis subsp. chloreasuis, Salmonella choleraesuis subsp. diarizonae, Salmonella choleraesuis subsp. houtenae, Salmonella choleraesuis subsp. indica, Salmonella choleraesuis subsp. salamae, Salmonella daressalaam, Salmonella enterica subsp. houtenae, Salmonella enterica subsp. salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens subsp. marcescens, Serratia marinorubra, Serratia odorifera, Serratia plymouthensis, Serratia plymuthica, Serratia proteamaculans, Serratia proteamaculans subsp. quinovora, Serratia quinivorans or Serratia rubidaea; Rhizobiaceae such as the genera Agrobacterium, Carbophilus, Chelatobacter, Ensifer, Rhizobium, Sinorhizobium for example the genera and species Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer

*saheli, Ensifer terangae, Ensifer xinjiangensis, Rhizobium ciceri Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli or Sinorhizobium xinjiangense.*

Further advantageous microorganisms for the process according to the invention are, for example, protists or diatoms selected from the group of the families Dinophyceae, Turaniellidae or Oxytrichidae, such as the genera and species: *Crypthecodinium cohnii, Phaeodactylum tricornutum, Stylonychia mytilus, Stylonychia pustulata, Stylonychia putrina, Stylonychia notophora, Stylonychia sp., Colpidium campylum* or *Colpidium* sp.

Organisms which are advantageously used in the process according to the invention are transgenic organisms such as fungi, such as *Mortierella* or *Traustochytrium*, yeasts such as *Saccharomyces* or *Schizosaccharomyces*, mosses such as *Physcomitrella* or *Ceratodon*, nonhuman animals such as *Caenorhabditis*, algae such as *Crypthecodinium* or *Phaeodactylum* or plants such as dicotyledonous or monocotyledonous plants. Organisms which are especially advantageously used in the process according to the invention are organisms which belong to the oil-producing organisms, that is to say which are used for the production of oils, such as fungi such as *Mortierella* or *Thraustochytrium*, algae such as *Crypthecodinium, Phaeodactylum* or plants, in particular plants, preferably, oil fruit crops which comprise large amounts of lipid compounds, such as peanut, oilseed rape, canola, sunflower, safflower, poppy, mustard, hemp, castor-oil plant, olive, sesame, *Calendula, Punica,* evening primrose, mullein, thistle, wild roses, hazelnut, almond, *macadamia,* avocado, bay, pumpkin/squash, linseed, soybean, pistachios, borage, trees (oil palm, coconut, walnut) or crops such as maize, wheat, rye, oats, triticale, rice, barley, cotton, cassava, pepper, Tagetes, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica,* evening primrose, pumpkin/squash, linseed, soybean, borage, trees (oil palm, coconut). Especially preferred are plants which are high in C18:2- and/or C18:3-fatty acids, such as sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

It is advantageous for the above-described process according to the invention to introduce, into the organism, further nucleic acids which encode enzymes of the fatty acid or lipid metabolism, in addition to the nucleic acid sequences introduced in the process which encode an ω-3-desaturase.

In principle, all genes of the fatty acid or lipid metabolism can be used in the process for the production of polyunsaturated fatty acids, advantageously in combination with the inventive ω-3-desaturase. Genes of the fatty acid or lipid metabolism selected from the group consisting of acyl-CoA dehydrogenase(s), acyl-ACP [=acyl carrier protein] desaturase(s), acyl-ACP thioesterase(s), fatty acid acyl transferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) are advantageously used in combination with the ω-3-desaturase. Genes selected from the group of the Δ4-desaturases, Δ5-desaturases, Δ6-desaturases, Δ8-desaturases, Δ9-desaturases, Δ12-desaturases, Δ5-elongases, Δ6-elongases or Δ9-elongases are especially preferably used in combination with the above genes for ω-3-desaturase, it being possible to use individual genes or a plurality of genes in combination.

In comparison with the known ω-3-desaturase, the ω-3-desaturase according to the invention has the advantageous characteristic that it is capable of desaturating a broad spectrum of ω-6-fatty acids, with $C_{20}$- and $C_{22}$-fatty acids such as $C_{20:2}$-, $C_{20:3}$-, $C_{20:4}$-, $C_{22:4}$- or $C_{22:5}$-fatty acids being preferentially desaturated. However, the shorter $C_{18}$-fatty acids such as $C_{18:2}$- or $C_{18:3}$-fatty acids are also advantageously desaturated. Owing to these characteristics of ω-3-desaturase, it is advantageously possible to shift the fatty acid spectrum within an organism, advantageously within a plant or a fungus, from the ω-6-fatty acids towards the ω-3-fatty acids. The ω-3-desaturase according to the invention preferentially desaturates $C_{20}$-fatty acids. Within the organism, these fatty acids are converted to at least 10%, 15%, 20%, 25% or 30% from the existing fatty acid pool to give the corresponding ω-3-fatty acids. In comparison with the $C_{18}$-fatty acids, the activity of ω-3-desaturase is lower by a factor of 10, that is to say only approximately 1.5 to 3% of the fatty acids present in the fatty acid pool are converted into the corresponding ω-3-fatty acids. Preferred substrates of the ω-3-desaturase according to the invention are the ω-6-fatty acids bound in phospholipids. With reference to the desaturation of dihomo-γ-linolenic acid [$C_{20:4}^{\Delta 8,11,14}$], FIG. 9 shows clearly that ω-3-desaturase advantageously does not differentiate between fatty acids bound at the sn1 or sn2 position when desaturation takes place. Both fatty acids bound at the sn1 position and fatty acids bound at the sn2 position in the phospholipids are desaturated. Another advantage is that ω-3-desaturase converts a broad range of phospholipids such as phosphatidylcholine (=PC), phosphatidylinositol (=PIS) or phosphatidylethanolamine (=PE). Finally, desaturation products are also found in the neutral lipids (=NL), i.e. in the triglycerides.

Owing to the enzymatic activity of the nucleic acids used in the process according to the invention which encode polypeptides with ω-3-desaturase activity, advantageously in combination with nucleic acid sequences which encode polypeptides of the fatty acid or lipid metabolism, such as additionally polypeptides with Δ4-, Δ5-, Δ6-, Δ8-desaturase or Δ5-, Δ6- or Δ9-elongase activity, a very wide range of polyunsaturated fatty acids can be produced in the process according to the invention. Depending on the choice of the organisms, such as the advantageous plant used for the process according to the invention, mixtures of the various polyunsaturated fatty acids or individual polyunsaturated fatty acids such as EPA or DHA can be produced in free or bound form. Depending on the prevailing fatty acid composition in the starting plant (C18:2- or C18:3-fatty acids), fatty acids which are derived from C18:2-fatty acids, such as GLA, DGLA or ARA, or which are derived from C18:3-fatty acids, such as SDA, ETA or EPA, are thus obtained. If only linoleic acid (=LA, $C18:2^{\Delta9,12}$) is present as unsaturated fatty acid in the plant used for the process, the process can only initially afford GLA, DGLA and ARA as products, all of which can be present as free fatty acids or in bound form. As a result of the activity of the ω-3-desaturase according to the invention, ω-3-fatty acids can eventually be synthesized from the above. If in the plant used in the process only α-linolenic acid (=ALA, $C18:3^{\Delta9,12,15}$) as unsaturated fatty acid, as is the case in flax, the process can only afford SDA, ETA, EPA and/or DHA as products, which, as described above, can be present as free fatty acids or in bound form. Owing to the modification of the activity of the enzyme ω-3-desaturase which plays a role in the synthesis, advantageously in combination with Δ4-, Δ5-, Δ6-desaturase and/or Δ6-elongase, and/or Δ5-elongase, or Δ4-, Δ5-, Δ8-desaturase, and/or Δ9-elongase and/or Δ5-elongase, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferentially formed. If Δ5-desaturase, Δ5-elongase and Δ4-desaturase are additionally introduced into the organisms, advantageously into the plant, ARA, EPA and/or DHA are additionally formed. This also applies to organisms into which Δ8-desaturase and Δ9-elongase have previously been introduced. Advantageously, only ARA, EPA or DHA or their mixtures, especially advantageously only EPA and DHA or their mixtures, are synthesized, depending on the fatty acid present in the organism or plant, which acts as starting substance for the synthesis. Since biosynthetic cascades are involved, the end products in question are not present in pure form in the organisms. Small amounts of the precursor compounds are always additionally present in the end product. These small amounts amount to less than 20% by weight, advantageously less than 15% by weight, especially advantageously less than 10% by weight, very especially advantageously less than 5, 4, 3, 2, or 1% by weight, based on the end product DGLA, ETA or their mixtures, or ARA, EPA, DHA or their mixtures, advantageously EPA or DHA or their mixtures.

In addition to the production directly in the organism of the starting fatty acids for the ω-3-desaturase according to the invention, the fatty acids can also be fed externally. The production in the organism is preferred for reasons of economy. Preferred substrates of ω-3-desaturase are linoleic acid ($C18:2^{\Delta9,12}$), γ-linolenic acid ($C_{18:3}^{\Delta6,9,12}$), eicosadienoic acid ($C20:2^{\Delta11,14}$), dihomo-γ-linolenic acid ($C20:3^{\Delta8,11,14}$) arachidonic acid ($C20:4^{\Delta5,8,11,14}$), docosatetraenoic acid ($C_{22:4}^{\Delta7,10,13,16}$) and docosapentaenoic acid ($C_{22:5}^{\Delta4,7,10,13,15}$).

To increase the yield in the above-described process for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which encodes a polypeptide with Δ12-desaturase activity. This is particularly advantageous in oil-producing organisms such as oilseed rape which are high in oleic acid. Since these organisms are only low in linoleic acid (Mikoklajczak et al., Journal of the American Oil Chemical Society, 38, 1961, 678-681), the use of the abovementioned Δ12-desaturases for producing the starting material linoleic acid is advantageous.

Nucleic acids used in the process according to the invention are advantageously derived from plants such as algae, for example *Isochrysis, Mantoniella, Ostreococcus* or *Crypthecodinium*, algae/diatoms such as *Phaeodactylum* or *Thraustochytrium*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, bacteria such as *Shewanella*, yeasts or animals such as nematodes such as *Caenorhabditis*, insects or fish. The isolated nucleic acid sequences according to the invention are advantageously derived from an animal of the order of the vertebrates. Preferably, the nucleic acid sequences are derived from the classes of the *Vertebrata; Euteleostomi, Actinopterygii; Neopterygii; Teleostei; Euteleostei, Protacanthopterygii, Salmoniformes*; Salmonidae or *Oncorhynchus*. The nucleic acids are especially advantageously derived from fungi, animals, or from plants such as algae or mosses, preferably from the order of the Salmoniformes, such as the family of the Salmonidae, such as the genus *Salmo*, for example from the genera and species *Oncorhynchus mykiss, Trutta trutta* or *Salmo trutta fario*, or from the diatoms such as the genera *Thallasiosira* or *Crypthecodinium*.

The process according to the invention advantageously employs the abovementioned nucleic acid sequences or their derivatives or homologs which encode polypeptides which retain the enzymatic activity of the proteins encoded by nucleic acid sequences. These sequences, individually or in combination with the nucleic acid sequences which encode ω-3-desaturase, are cloned into expression constructs and used for the introduction into, and expression in, organisms. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with a nucleic acid sequence according to the invention which encodes the ω-3-desaturase, a gene construct or a vector as described below, alone or in combination with further nucleic acid sequences which encode proteins of the fatty acid or lipid metabolism. In a further preferred embodiment, this process furthermore comprises the step of obtaining the oils, lipids or free fatty acids from the organism or the culture. The culture may, for example, take the form of a fermentation culture, for example in the case where microorganisms such as, for example, *Mortierella, Saccharomyces* or *Thraustochytrium* are cultured, or the form of a greenhouse or field-grown culture of a plant. The cell thus produced, or the organism thus produced, is advantageously a cell of an oil-producing organism, such as an oil crop, such as, for example, peanut, oilseed rap, canola, linseed, hemp, peanut, soybean, safflower, hemp, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

For the purposes of the invention, "transgenic" or "recombinant" means with regard to, for example, a nucleic acid sequence an expression cassette (=gene construct) or a vector comprising the nucleic acid sequence according to the invention or an organism transformed with the nucleic acid sequences, expression cassette or vector according to the invention, all those constructions brought about by recombinant methods in which either
a) the nucleic acid sequence according to the invention, or
b) a genetic control sequence which is operably linked with the nucleic acid sequence according to the invention, for example a promoter, or
c) a) and b)
are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original organism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences according to the invention with the corresponding ω-3-desaturase genes—becomes a transgenic expression cassette when this expression cassette is modified by unnatural, synthetic ("artificial") methods such as, for example, mutagenic treatment. Suitable methods are described, for example, in U.S. Pat. No. 5,565,350 or WO 00/15815.

Transgenic organism or transgenic plant for the purposes of the invention is, as mentioned above, understood as meaning that the nucleic acids used in the process are not at their natural locus in the genome of an organism, it being possible for the nucleic acids to be expressed homologously or heterologously. However, transgenic also means that, as mentioned above, while the nucleic acids according to the invention are at their natural position in the genome of an organism, however, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic organisms are fungi such as *Mortierella*, mosses such as *Physcomitrella*, algae such as *Crypthecodinium* or plants such as the oil crop plants.

Suitable organisms, or host organisms, for the nucleic acids, the expression cassette or the vector used in the process according to the invention are advantageously in principle all those organisms which are capable of synthesizing fatty acids, specifically unsaturated fatty acids, or which are suitable for the expression of recombinant genes. Examples which may be mentioned are plants such as Brassicaceae, such as *Arabidopsis*, Asteraceae such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms such as fungi, for example the genus *Mortierella*, *Thraustochytrium*, *Saprolegnia* or *Pythium*, bacteria such as the genus *Escherichia* or *Shewanella*, yeasts such as the genus *Saccharomyces*, cyanobacteria, ciliates, algae or protozoans such as dinoflagellates, such as *Cryptheco-* *dinium*. Organisms which are naturally capable of synthesizing large amounts of oils are preferred, such as fungi such as *Mortierella alpina, Pythium insidiosum* or plants such as soybean, oilseed rape, coconut, oil palm, safflower, flax, hemp, castor-oil plant, *Calendula*, peanut, cacao bean or sunflower, or yeasts such as *Saccharomyces cerevisiae*, with soybean, flax, oilseed rape, safflower, sunflower, *Calendula*, *Mortierella* or *Saccharomyces cerevisiae* being especially preferred. In principle, transgenic animals, advantageously nonhuman animals, for example *C. elegans*, are also suitable as host organisms, in addition to the abovementioned transgenic organisms.

Host cells which can be exploited are furthermore mentioned in: Goeddel, Gene Expression Technology: Methods in Enzymology 185, Academic Press, San Diego, Calif. (1990).

Expression strains which can be used, for example those with a lower protease activity, are described in: Gottesman, S., Gene Expression Technology: Methods in Enzymology 185, Academic Press, San Diego, Calif. (1990) 119-128.

These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which is derived from the actual transgenic plant and/or can be used for bringing about the transgenic plant.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are understood as meaning intact plants and all plant parts, plant organs or plant parts such as leaf, stem, seed, root, tubers, anthers, fibers, root hairs, stalks, embryos, calli, cotelydons, petioles, harvested material, plant tissue, reproductive tissue and cell cultures which are derived from the transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously the plants, in the form of their oils, fat, lipids and/or free fatty acids. Polyunsaturated fatty acids produced by this process can be harvested by harvesting the organisms either from the culture in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat by pressing. To allow for greater ease of disruption of the plant parts, specifically the seeds, they are previously comminuted, steamed or roasted. The seeds which have been pretreated in this manner can subsequently be pressed or extracted with solvent such as warm hexane. The solvent is subsequently removed again. In the case of microorganisms, for example, these are harvested and then extracted directly without further processing steps, or else disrupted and then extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as deslimming can be effected enzymatically or, for example, chemicophysically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigment remaining in the product, the products are subjected to bleaching, for example using fuller's earth or active charcoal. At the end, the product is deodorized, for example using steam.

The PUFAs or LCPUFAs produced by this process are preferably $C_{18}$-, $C_{20}$- or $C_{22}$-fatty acid molecules with at least two double bonds in the fatty acid molecule, preferably with two, three, four, five or six double bonds. These $C_{18}$-, $C_{20}$- or $C_{22}$-fatty acid molecules can be isolated from the organism in the form of an oil, a lipid or a free fatty acid. Examples of suitable organisms are those mentioned above. Preferred organisms are transgenic plants.

One embodiment of the invention are therefore oils, lipids or fatty acids or fractions thereof which have been prepared by the above-described process, especially preferably oil, lipid or a fatty acid composition which comprise PUFAs and originate from transgenic plants.

As described above, these oils, lipids or fatty acids advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acid which is present in the fatty acid esters or fatty acid mixtures is preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernonic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The fatty acid esters or fatty acid mixtures produced by the process according to the invention advantageously comprise less than 0.1%, based on the total fatty acids, or no butter butyric acid, no cholesterol, no clupanodonic acid (=dpcpsapentaenoic acid, $C22:5^{\Delta 4,8,12,15,21}$) and no nisinic acid (tetracosahexaenoic acid, $C23:6^{\Delta 3,8,12,15,18,21}$).

The oils, lipids or fatty acids according to the invention advantageously comprise at least 0.5%, 1%, 2%, 3%, 4% or 5%, advantageously at least 6%, 7%, 8%, 9% or 10%, especially advantageously at least 11%, 12%, 13%, 14% or 15% of ARA or at least 0.5%, 1%, 2%, 3%, 4% or 5%, advantageously at least 6% or 7%, especially advantageously at least 8%, 9% or 10% of EPA and/or of DHA, based on the total fatty acid content of the production organism, advantageously of a plant, especially advantageously of an oil crop such as soybean, oilseed rape, coconut, oil palm, safflower, flax, hemp, castor-oil plant, *Calendula*, peanut, cacao bean, sunflower or the abovementioned other monocotyledonous or dicotyledonous oil crops.

A further embodiment according to the invention is the use of the oil, lipid, fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin such as, for example, fish oils.

The term "oil", "lipid" or "fat" is understood as meaning a fatty acid mixture comprising unsaturated or saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds, which acids are produced in the process, are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least five or six double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains which also accumulate PUFAs in the triacylglycerol fraction are particularly advantageous for the process according to the invention and thus for the modification of the lipid and PUFA production system in a host, in particular plants such as oil crops, for example oilseed rape, canola, linseed, hemp, soybean, sunflowers and borage. They can therefore be used advantageously in the process according to the invention.

Substrates which are advantageously suitable for the nucleic acids which are used in the process according to the invention and which encode polypeptides with ω-3-desaturase activity and/or the further nucleic acids used, such as the nucleic acids which encode polypeptides of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA: lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allenoxide synthase(s), hydroperoxide lyase(s) or fatty acid elongase(s) are $C_{18}$-, $C_{20}$- or $C_{22}$-fatty acids. The fatty acids converted as substrates in the process are preferably converted in the form of their phospholipid esters.

To produce the long-chain PUFAs according to the invention, the polyunsaturated $C_{18}$-fatty acids must first be desaturated by the enzymatic activity of a desaturase and subsequently be elongated by at least two carbon atoms via an elongase. After one elongation cycle, this enzyme activity gives $C_{20}$-fatty acids and after two elongation cycles $C_{22}$-fatty acids. The activity of the desaturases and elongases used in the process according to the invention preferably leads to $C_{18}$-, $C_{20}$- and/or $C_{22}$-fatty acids, advantageously with at least two double bonds in the fatty acid molecule, preferably with three, four, five or six double bonds, especially preferably to give $C_{20}$- and/or $C_{22}$-fatty acids with at least two double bonds in the fatty acid molecule, preferably with three, four, five or six double bonds, very especially preferably with four, five or six double bonds in the molecule. After a first desaturation and the elongation have taken place, further desaturation and elongation steps, for example such a desaturation in the Δ5 and Δ4 positions, may take place. Products of the process according to the invention which are especially preferred are eicosatrienoic acid, eicosapentaenoic acid, docosapentaenoic acid and/or docosahexaenoic acid. The $C_{20}$-fatty acids with at least two double bonds in the fatty acid can be elongated by the enzymatic activity of the enzymes used in the process in the form of the free fatty acid or in the form of the esters, such as phospholipids, glycolipids, sphingolipids, phosphoglycerides, monoacylglycerol, diacylglycerol or triacylglycerol.

The preferred biosynthesis site of fatty acids, oils, lipids or fats in the plants which are advantageously used is, for example, in general the seed or cell strata of the seed, so that seed-specific expression of the nucleic acids used in the process makes sense. However, it is obvious that the biosynthesis of fatty acids, oils or lipids need not be limited to the seed tissue, but can also take place in a tissue-specific manner in all the other parts of the plant, for example in epidermal cells or in the tubers.

If, in the process according to the invention, microorganisms such as yeasts, such as *Saccharomyces* or *Schizosaccharomyces*, fungi such as *Mortierella, Aspergillus, Phytophthora, Entomophthora, Mucor* or *Thraustochytrium*, algae such as *Isochrysis, Phaeodactylum* or *Cryptheco-dinium* are used as organisms, these organisms are preferably cultured in a fermentation.

Owing to the use of the nucleic acids according to the invention which encode a ω-3-desaturase, the polyunsaturated fatty acids produced in the process can be increased by at least 5%, preferably by at least 10%, especially preferably by at least 20%, very especially preferably by at least 50% in comparison with the wild type of the organisms which do not comprise the nucleic acids recombinantly.

In principle, the polyunsaturated fatty acids produced by the process according to the invention in the organisms used in the process can be increased in two ways. The pool of free polyunsaturated fatty acids and/or the content of the esterified polyunsaturated fatty acids produced via the process can be advantageously enlarged. Advantageously, the pool of esterified polyunsaturated fatty acids in the transgenic organisms is enlarged by the process according to the invention.

If microorganisms are used as organisms in the process according to the invention, they will be cultured, or grown, in the manner with which the skilled worker is familiar, depending on the host organism. As a rule, microorganisms will be grown in a liquid medium comprising a carbon source, mostly in the form of sugars, a nitrogen source, mostly in the form of organic nitrogen sources such as yeast extract or salts such as ammonium sulfate, trace elements such as iron, manganese and magnesium salts, and, if appropriate, vitamins, at temperatures between 0° C. and 100° C., preferably between 10° C. to 60° C., while gassing in oxygen. During this process, the pH of the liquid nutrient may be kept constant, i.e. regulated during the culture period, or not. The culture can be effected batchwise, semibatchwise or continuously. Nutrients can be introduced at the beginning of the fermentation or fed in semicontinuously or continuously. The polyunsaturated fatty acids produced can be isolated from the organisms by methods with which the skilled worker is familiar, as described above; for example via extraction, distillation, crystallization, if appropriate salt precipitation and/or chromatography. To do so, the organisms can advantageously be disrupted beforehand.

If the host organisms take the form of microorganisms, the process according to the invention is advantageously carried out at a temperature of between 0° C. to 95° C., preferably between 10° C. to 85° C., especially preferably between 15° C. to 75° C., very especially preferably between 15° C. to 45° C.

The pH is advantageously maintained at between pH 4 and pH 12, preferably between pH 6 and pH 9, especially preferably between pH 7 and pH 8.

The process according to the invention can be carried out batchwise, semibatchwise or continuously. A summary of known cultivation methods is to be found in the textbook by Chmiel (Bioprozeβtechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy in a suitable manner the demands of the respective strains. There are descriptions of culture media for various microorganisms in the handbook "Manual of Methods for General Bacteriology" of the American Society for Bacteriology (Washington D.C., USA, 1981).

These media which can be employed according to the invention usually comprise one or more carbon sources, nitrogen sources, inorganic salts, vitamins and/or trace elements, as described above.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch or cellulose. Sugars can be put in the media also via complex compounds such as molasses, or other by-products of sugar refining. It may also be advantageous to add mixtures of various carbon sources. Other possible carbon sources are oils and fats such as, for example, soybean oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol and/or organic acids such as, for example, acetic acid and/or lactic acid.

Nitrogen sources are usually organic or inorganic nitrogen compounds or materials comprising these compounds. Examples of nitrogen sources include ammonia gas, ammonia liquid or ammonium salts such as ammonium sulfate, ammonium chloride, ammonium phosphate, ammonium carbonate or ammonium nitrate, nitrates, urea, amino acids or complex nitrogen sources such as corn steep liquor, soybean flour, soybean protein, yeast extract, meat extract and others. The nitrogen sources may be used singly or as mixtures.

Inorganic salt compounds which may be present in the media comprise the chloride, phosphoric or sulfate salts of calcium, magnesium, sodium, cobalt, molybdenum, potassium, manganese, zinc, copper and iron.

For producing sulfur-containing fine chemicals, especially methionine, it is possible to use as sulfur source inorganic sulfur-containing compounds such as, for example, sulfates, sulfites, dithionites, tetrathionates, thiosulfates, sulfides, but also organic sulfur compounds such as mercaptans and thiols.

It is possible to use as phosphorus source phosphoric acid, potassium dihydrogenphosphate or dipotassium hydrogenphosphate or the corresponding sodium-containing salts.

Chelating agents can be added to the medium in order to keep the metal ions in solution. Particularly suitable chelating agents comprise dihydroxyphenols such as catechol or protocatechuate, or organic acids such as citric acid.

The fermentation media employed according to the invention for the culture of microorganisms normally also comprise other growth factors such as vitamins or growth promoters, which include for example biotin, riboflavin, thiamine, folic acid, nicotinic acid, pantothenate and pyridoxine. Growth factors and salts are frequently derived from complex components of the media, such as yeast extract, molasses, corn steep liquor and the like. Suitable precursors may also be added to the culture medium. The exact composition of the compounds in the media depends greatly on the particular experiment and will be decided individually for each specific case. Information on optimization of media is obtainable from the textbook "Applied Microbiol. Physiology, A Practical Approach" (editors P. M. Rhodes, P. F. Stanbury, IRL Press (1997) pp. 53-73, ISBN 0 19 963577 3). Growth media can also be purchased from commercial suppliers, such as Standard 1 (Merck) or BHI (Brain heart infusion, DIFCO) and the like.

All the components of the media are sterilized either by heat (20 min at 1.5 bar and 121° C.) or by filter sterilization. The components can be sterilized either together or, if necessary, separately. All the components of the media may be present at the start of culturing or optionally be added continuously or batchwise.

The temperature of the culture is normally between 15° C. and 45° C., preferably at 25° C. to 40° C., and can be kept constant or changed during the experiment. The pH of the medium should be in the range from 5 to 8.5, preferably around 7.0. The pH for the culturing can be controlled during the culturing by adding basic compounds such as sodium hydroxide, potassium hydroxide, ammonia or aqueous ammonia or acidic compounds such as phosphoric acid or sulfuric acid. The development of foam can be controlled by employing antifoams such as, for example, fatty acid polyglycol esters. The stability of plasmids can be maintained by adding to the medium suitable substances with a selective action, such as, for example, antibiotics. Aerobic conditions are maintained by introducing oxygen or oxygen-containing gas mixtures such as, for example, ambient air into the culture. The temperature of the culture is normally 20° C. to 45° C., and preferably 25° C. to 40° C. The culture is continued until formation of the desired product is at a maximum. This aim is normally reached within 10 hours to 160 hours.

The dry matter content of the fermentation broths obtained in this way and comprising in particular polyunsaturated fatty acids is normally from 7.5 to 25% by weight.

The fermentation broth can then be processed further. Depending on the requirement, the biomass can be removed wholly or partly from the fermentation broth by separation methods such as, for example, centrifugation, filtration, decantation or a combination of these methods, or left completely in it. The biomass is advantageously worked up after removal.

However, the fermentation broth can also be thickened or concentrated by known methods such as, for example, with the aid of a rotary evaporator, thin-film evaporator, falling-film evaporator, by reverse osmosis or by nanofiltration, without involving a cell removal step. This concentrated fermentation broth can then be worked up to obtain the fatty acids comprised therein.

The fatty acids obtained in the process are also suitable as starting material for the chemical synthesis of further products of value. For example, they can be used in combination with one another or individually for the preparation of pharmaceuticals, foodstuffs, animal feed or cosmetics.

The nucleic acid sequences which are used in the process and which encode proteins with ω-3-desaturase activity are, alone or preferably in combination with further fatty acid biosynthesis genes, advantageously introduced into an expression cassette (=nucleic acid construct) which makes possible the expression of the nucleic acids in an organism, advantageously a plant or a microorganism.

For the introduction, the nucleic acids used in the process are advantageously subjected to amplification and ligation in the known manner. It is preferable to follow a procedure similar to the protocol of the Pfu-DNA polymerase or of a Pfu/Taq-DNA polymerase mixture. The primers are chosen to suit the sequence to be amplified. The primers should expediently be chosen in such a way that the amplificate comprises the entire codogenic sequence from the start codon to the stop codon. After the amplification, it is expedient to analyze the amplificate. For example, it can be separated by gel electrophoresis and then analyzed with regard to quality and quantity. Thereafter, the amplificate can be purified following a standard protocol (for example Qiagen). An aliquot of the purified amplificate is now available for the subsequent cloning step. Suitable cloning vectors are generally known to the skilled worker. These include, in particular, vectors which are replicable in microbial systems, that is to say mainly vectors which ensure efficient cloning in yeasts or fungi and which make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems preferably also comprise further cis-regulatory regions such as promoters and terminators and/or selection markers with which suitable transformed organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. To prepare the vector, the vectors can first be linearized with the aid of restriction endonuclease(s) and then suitably modified by enzymatic means. Thereafter, the vector is purified, and an aliquot is employed for the cloning step. For the cloning, the enzymatically cleaved and, if appropriate, purified amplificate is cloned together with similarly prepared vector fragments, using ligase. Here, a specific nucleic acid construct, or vector or plasmid construct, may have one or else more than one codogenic gene segment. The codogenic gene segments in these constructs are preferably linked operably with regulatory sequences. The regulatory sequences include, in particular, plant sequences such as the above-described promoters and terminators. The constructs can advantageously be propagated stably under selective conditions in microorganisms, in particular *Escherichia coli* and *Agrobacterium tumefaciens*, and make possible the transfer of heterologous DNA into plants or microorganisms.

With the advantageous use of cloning vectors, the nucleic acids used in the process, the inventive nucleic acids and nucleic acid constructs can be introduced into organisms such as microorganisms or, advantageously, plants, and thus be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. The nucleic acids used in the process, the inventive nucleic acids and nucleic acid constructs and/or vectors, can thus be used for the recombinant modification of a broad spectrum of organisms, advantageously plants, so that the latter become better and/or more efficient PUFA producers.

A series of mechanisms exist which enable a modification of the ω-3-desaturase protein according to the invention and of the further proteins used in the process, such as the Δ9-elongase, Δ6-desaturase, Δ8-desaturase, Δ6-elongase, Δ5-desaturase, Δ5-elongase or Δ4-desaturase proteins, so that the yield, production and/or production efficiency of the advantageously polyunsaturated fatty acids in a plant, preferably in an oil crop or a microorganism, can be influenced directly as a result of this modified protein. The number or activity of the Δ9-elongase, Δ6-desaturase, Δ8-desaturase, Δ6-elongase, Δ5-desaturase, Δ5-elongase, Δ4-desaturase or ω-3-desaturase proteins or genes can be increased so that larger amounts of the gene products and thus ultimately larger amounts of the compounds of the general formula I are produced. A de-novo synthesis in an organism which had lacked the activity and ability to biosynthesize the compounds prior to the introduction of the gene(s) in question is also possible. The same applies to the combination with further desaturases or elongases or further enzymes from the fatty acid and lipid metabolism. Also, the use of different, divergent sequences, i.e. sequences which differ at the DNA sequence level, may be advantageous, or the use of promoters for gene expression which makes possible a different clock-dependent gene expression, for example depending on the degree of maturity of a seed or oil-storing tissue.

Introducing a Δ9-elongase, Δ6-desaturase, Δ8-desaturase, Δ6-elongase, Δ5-desaturase, Δ5-elongase, Δ4-desaturase and/or ω-3-desaturase gene into an organism alone or in combination with other genes into a cell may not only increase the biosynthetic flux towards the end product, but also increase the corresponding triacylglycerol composition or create it de novo. Likewise, the number or activity of other genes in the import of nutrients required for the biosynthesis of one or more fatty acids, oils, polar and/or neutral lipids may be increased, so that the concentration of these precursors, cofactors or intermediates within the cells or within the storage compartment is increased, whereby the ability of the cells to produce PUFAs is increased further, as described hereinbelow. By optimizing the activity or increasing the number of one or more Δ9-elongase, Δ6-desaturase, Δ8-desaturase, Δ6-elongase, Δ5-desaturase, Δ5-elongase, Δ4-desaturase or ω-3-desaturase genes which are involved in the biosynthesis of these compounds, or by destroying the activity of one or more genes which are involved in breaking down these compounds, it may be possible to increase the yield, production and/or production efficiency of fatty acid and lipid molecules from organisms and advantageously from plants.

The isolated nucleic acid molecules used in the process according to the invention encode proteins or parts of these, the proteins or the individual protein or parts thereof comprising an amino acid sequence with sufficient homology with an amino acid sequence which is shown in the sequences SEQ ID NO: 2 so that the proteins or parts thereof retain a ω-3-desaturase activity. The proteins or parts thereof, which is/are encoded by the nucleic acid molecule(s), preferably still retain their essential enzymatic activity and the ability of participating in the metabolism of compounds required in the formation of cell membranes or lipid bodies in organisms, advantageously in plants, or in the transport of molecules across these membranes. Advantageously, the proteins encoded by the nucleic acid molecules have at least approximately 60%, preferably at least approximately 70% and more preferably at least approximately 80% or 90% and most preferably at least approximately 95%, 96%, 97%, 98%, 99% or more identity with the amino acid sequence shown in SEQ ID NO: 2. For the purposes of the invention, homology or homologous is understood as meaning identity or identical.

The homology was calculated over the entire amino acid or nucleic acid sequence region. A series of programs which are based on the various algorithms are available to those skilled in the art for comparing different sequences. In this context, the algorithms of Needleman and Wunsch or Smith and Waterman give especially reliable results. To carry out the sequence alignments, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981)), which are part of the GCG software packet [Genetics Computer Group, 575 Science Drive, Madison, Wis., USA 53711 (1991)], were used. The sequence homology values stated above as percentages were determined over the entire sequence region using the program GAP, with the following settings: Gap Weight: 50, Length Weight: 3, Average Match: 10.000 and Average Mismatch: 0.000. Unless otherwise specified, these settings were always used as standard settings for sequence alignments.

Essential enzymatic activity of the ω-3-desaturase used in the process according to the invention is understood as meaning that, in comparison with the proteins/enzymes encoded by the sequence SEQ ID NO: 1 and their derivatives, it retain at least an enzymatic activity of at least 10%, preferably 20%, especially preferably 30% and very especially 40% and can thus participate in the metabolism of compounds required in the synthesis of fatty acids, fatty acid esters such as diacylglycerides and/or triacylglycerides in an organism, advantageously a plant or plant cell, or in the transport of molecules across membranes, meaning $C_{18}$-, $C_{20}$- or $C_{22}$-carbon chains in the fatty acid molecule with double bonds at at least two, advantageously three, four, five or six positions.

Nucleic acids which can be used advantageously in the process are derived from bacteria, fungi, diatoms, animals such as *Caenorhabditis* or plants such as algae or mosses, such as the genera *Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Phaeodactylum tricornutum* or *Caenorhabditis elegans* or especially advantageously *Phytophtora infestans, Thallasiosira pseudonona* or *Cryptocodinium cohnii*.

As an alternative, it is possible to use, in the process according to the invention, nucleotide sequences which encode ω-3-desaturase and which hybridize, advantageously under stringent conditions, with a nucleotide sequence as shown in SEQ ID NO: 1.

The nucleic acid sequences used in the process are advantageously introduced in an expression cassette which enables the expression of the nucleic acids in organisms such as microorganisms or plants.

In this context, the nucleic acid sequences which encode the ω-3-desaturase are advantageously linked functionally with one or more regulatory signals to increase gene expression. These regulatory sequences should enable the targeted expression of the genes and protein expression. For example, this may mean, depending on the host organism, that the gene is expressed and/or overexpressed only after induction has taken place, or else that it is expressed and/or overexpressed immediately. For example, these regulatory sequences take the form of sequences to which inductors or repressors bind and thus regulate the expression of the nucleic acid. In addition to these new regulatory sequences, or instead of these sequences, the natural regulation of these sequences may still be present before the actual structural genes and, if appropriate, may have been genetically modified in such a way that the natural regulation has been switched off and the expression of the genes enhanced. The expression cassette (=expression construct=gene construct) may, however, also be simpler in construction, that is to say no additional regulatory signals were inserted before the nucleic acid sequence or its derivatives, and the natural promoter together with its regulation was not removed. Instead, the natural regulatory sequence was mutated in such a way that regulation no longer takes place and/or gene expression is enhanced. These modified promoters can be placed before the natural gene in order to increase the activity either in the form of part-sequences (=promoter with parts of the nucleic acid sequences according to the invention) or else alone. Moreover, the gene construct can advantageously also comprise one or more what are known as "enhancer sequences" in functional linkage with the promoter, and these enable an increased expression of the nucleic acid sequence. Also, it is possible to insert additional advantageous sequences at the 3' end of the DNA sequences, such as further regulatory elements or terminators. The ω-3-desaturase genes can be present in the expression cassette (=gene construct) as one or more copies. The same applies to the other fatty acid biosynthesis genes which are used in combination with the. ω-3-desaturase according to the invention. Advantageously, only in each case one copy of the genes is present in the expression cassette. This gene construct, or the gene constructs, can be expressed together in the host organism. In this context, the gene construct(s) can be inserted in one or more vectors and be present in the cell in free form or else inserted in the genome. It is advantageous for the insertion of further genes in the host genome when the genes to be expressed are present together in one gene construct.

In this context, the regulatory sequences or factors can, as described above, preferably have a positive effect on the gene expression of the genes which have been introduced, thus increasing it. Thus, enhancement of the regulatory elements can advantageously take place at the transcription level by using strong transcription signals such as promoters and/or enhancers. Besides, however, an enhancement of the translation is also possible, for example by improving the stability of the mRNA.

A further embodiment of the invention are one or more gene constructs which comprise one or more sequences which are defined by SEQ ID NO: 1 or its derivatives and code for polypeptides according to SEQ ID NO: 2. The abovementioned ω-3-desaturase proteins advantageously result in a desaturation of ω-6-fatty acids, the substrate advantageously having two, three, four or five double bonds and advantageously 18, 20 or 22 carbon atoms in the fatty acid molecule. The same applies to their homologs, derivatives or analogs which are linked operably with one or more regulatory signals, advantageously for increasing gene expression.

Advantageous regulatory sequences for the novel process are present for example in promoters such as the cos, tac, trp, tet, trp-tet, lpp, lac, lpp-lac, lacIq, T7, T5, T3, gal, trc, ara, SP6, λ-PR or λ-PL promoter and are advantageously used in Gram-negative bacteria. Further advantageous regulatory sequences are present for example in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Also advantageous in this context are inducible promoters, such as the promoters described in EP-A-0 388 186 (benzylsulfonamide-inducible), Plant J. 2, 1992:397-404 (Gatz et al., tetracyclin-inducible), EP-A-0 335 528 (abscisic-acid-inducible) or WO 93/21334 (ethanol- or cyclohexenol-inducible). Further suitable plant promoters are the promoter of cytosolic FBPase or the ST-LSI promoter from potato (Stockhaus et al., EMBO J. 8, 1989, 2445), the phosphoribosyl-pyrophosphate amidotransferase promoter from *Glycine max* (Genbank accession No. U87999) or the node-specific promoter described in EP-A-0 249 676. Especially advantageous promoters are promoters which enable the expression in tissues which are involved in the biosynthesis of fatty acids. Very especially advantageous are seed-specific promoters such as the USP promoter in accordance with the practice, but also other promoters such as the LeB4, DC3, phaseolin or napin promoters. Further especially advantageous promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arobidopsis*, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for example for monocots: lpt-2 or lpt-1 promoter from barley (WO 95/15389 and WO 95/23230), hordein promoter from barley and other promoters which are suitable and which are described in WO 99/16890.

In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890.

To obtain a particularly high PUFA content especially in transgenic plants, the ω-3-desaturase and/or PUFA biosynthesis genes should advantageously be expressed in a seed-specific manner in oilseed crops. To this end, it is possible to use seed-specific promoters or those promoters which are active in the embryo and/or in the endosperm. In principle, seed-specific promoters can be isolated both from dicotyledonous and from monocotyledonous plants. Advantageous preferred promoters are listed hereinbelow: USP (=unknown seed protein) and vicilin (*Vicia faba*) [Bäumlein et al., Mol. Gen. Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], Legume B4 (LegB4 promoter) [Bäumlein et al., Plant J., 2,2, 1992], Lpt2 and lpt1 (barley) [WO 95/15389 und WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol-pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

The expression of plant genes can also be facilitated via a chemically inducible promoter (for a review see Gatz 1997, Annu. Rev. Plant Physiol. Plant Mol. Biol., 48:89-108). Chemically inducible promoters are particularly suitable when it is desired that gene expression is effected in a clock-controlled manner. Examples of such promoters are salicylic-acid-inducible promoter (WO 95/19443), a tetracyclin-inducible promoter (Gatz et al. (1992) Plant J. 2, 397-404) and an ethanol-inducible promoter.

To ensure a stable integration of the biosynthetic genes into the transgenic plant over a plurality of generation, each of the nucleic acids used in the process which encode the ω-3-desaturase gene or further fatty acid biosynthesis genes such as Δ9-elongase, Δ6-desaturase, Δ8-desaturase, Δ6-elongase, Δ5-desaturase, Δ5-elongase and/or Δ4-desaturase should be expressed under the control of a separate promoter, preferably a different promoter, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and then, if appropriate, a terminator is positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator. Such advantageous constructs are disclosed, for example, in DE 101 02 337 or DE 101 02 338 (see, for example, in the appended sequence listings). However, it is also possible to insert a plurality of nucleic acid sequences behind a promoter and, if appropriate, before a terminator. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator can be used in the expression cassette. However, it is also possible to use only one type of promoter in the cassette, which, however, may lead to undesired recombination events.

As described above, the transcription of the genes which have been introduced should advantageously be terminated by suitable terminators at the 3' end of the biosynthesis genes which have been introduced (behind the stop codon). An example of a sequence which can be used in this context is the OCS1 terminator. As is the case with the promoters as well, different terminator sequences should be used for each gene.

As described above, the gene construct can also comprise further genes to be introduced into the organisms. It is possible and advantageous to introduce into the host organisms, and to express therein, regulatory genes such as genes for inductors, repressors or enzymes which, owing to their enzyme activity, engage in the regulation of one or more genes of a biosynthetic pathway. These genes can be of heterologous or of homologous origin. Moreover, further biosynthesis genes of the fatty acid or lipid metabolism can advantageously be present in the nucleic acid construct, or gene construct; however, these genes can also be present on one or more further nucleic acid constructs. A biosynthesis gene of the fatty acid or lipid metabolism which is preferably chosen is a gene from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allenoxide synthase(s), hydroperoxide lyase(s) or fatty acid elongase(s) or combinations thereof. Especially advantageous nucleic acid sequences are biosynthesis genes of the fatty acid or lipid metabolism selected from the group of the acyl-CoA:lysophospholipid acyltransferase, $\Delta 4$-desaturase, $\Delta 5$-desaturase, $\Delta 6$-desaturase, $\Delta 8$-desaturase, $\Delta 9$-desaturase, $\Delta 12$-desaturase, $\Delta 5$-elongase, $\Delta 6$-elongase and/or $\Delta 9$-elongase.

In this context, the abovementioned nucleic acids or genes can be cloned into expression cassettes, like those mentioned above, in combination with other elongases and desaturases and used for transforming plants with the aid of *Agrobacterium*.

Here, the regulatory sequences or factors can, as described above, preferably have a positive effect on, and thus enhance, the gene expression of the genes which have been introduced. Thus, enhancement of the regulatory elements can advantageously take place at the transcriptional level by using strong transcription signals such as promoters and/or enhancers. However, an enhanced translation is also possible, for example by improving the stability of the mRNA. In principle, the expression cassettes can be used directly for introduction into the plants or else be introduced into a vector.

These advantageous vectors, preferably expression vectors, comprise the nucleic acids according to the invention which encode ω-3-desaturases, which acids are used in the process, and, if appropriate, further nucleic acids which are used in the process and which encode $\Delta 9$-elongases, $\Delta 6$-desaturases, $\Delta 8$-desaturases, $\Delta 6$-elongases, $\Delta 5$-desaturases, $\Delta 5$-elongases or $\Delta 4$-desaturases or else a nucleic acid construct which comprises the nucleic acid used either alone or in combination with further biosynthesis genes of the fatty acid or lipid metabolism such as the acyl-CoA:lysophospholipid acyltransferases, $\Delta 4$-desaturases, $\Delta 5$-desaturases, $\Delta 6$-desaturases, $\Delta 8$-desaturases, $\Delta 9$-desaturases, $\Delta 12$-desaturases, ω-3-desaturases, $\Delta 5$-elongases, $\Delta 6$-elongases and/or $\Delta 9$-elongases. As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is also intended to cover other forms of expression vectors, such as viral vectors, which exert similar functions. Furthermore, the term "vector" is also intended to encompass other vectors with which the skilled worker is familiar, such as phages, viruses such as SV40, CMV, TMV, transposons, IS elements, phasmids, phagemids, cosmids, linear or circular DNA.

The recombinant expression vectors advantageously used in the process comprise the above described nucleic acid sequences and/or the above described gene construct in a form which is suitable for expressing the nucleic acids used in a host cell, which means that the recombinant expression vectors comprises one or more regulatory sequences, selected on the basis of the host cells used for the expression, which regulatory sequence(s) is/are linked operably with the nucleic acid sequence to be expressed. In a recombinant expression vector, "linked operably" means that the nucleotide sequence of interest is bound to the regulatory sequence(s) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the desired expression level of the protein and the like.

The recombinant expression vectors used can be designed for expressing ω-3-desaturases, $\Delta 9$-elongases, $\Delta 6$-desaturases, $\Delta 8$-desaturases, $\Delta 6$-elongases, $\Delta 5$-desaturases, $\Delta 5$-elongases and/or $\Delta 4$-desaturases in prokaryotic or eukaryotic cells. This is advantageous since, for the sake of simplicity, intermediate steps of the vector construction are frequently carried out in microorganisms. For example, the ω-3-desaturase, $\Delta 9$-elongase, $\Delta 6$-desaturase, $\Delta 8$-desaturase, $\Delta 6$-elongase, $\Delta 5$-desaturase, $\Delta 5$-elongase and/or $\Delta 4$-desaturase genes can be expressed in bacterial cells, insect cells (using baculovirus expression vectors), yeast cells and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular the genus *Stylonychia lemnae*, using vectors following a transformation process as described in WO 98/01572, and preferably in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant Molecular Biology and Biotechnology, C Press, Boca Raton, Fla., chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes is performed using vectors comprising constitutive or inducible promoters which control the expression of fusion or nonfusion proteins. Examples of typical fusion expression vectors are pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter.

The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennett & L. L. Lasure, Ed., pp. 396-428: Academic Press: San Diego]. Further suitable yeast vectors are, for example, pAG-1, YEp6, YEp13 or pEMBLYe23.

As an alternative, the ω-3-desaturases, Δ9-elongases, Δ6-desaturases, Δ8-desaturases, Δ6-elongases, Δ5-desaturases, Δ5-elongases and/or Δ4-desaturases can be expressed in insect cells using baculovirus expression vectors. Baculovirus vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

The abovementioned vectors are only a small overview of possible suitable vectors. Further plasmids are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells, see the chapters 16 and 17 of Sambrook, J., Fritsch, E. F., and Maniatis, T., Molecular Cloning: A Laboratory Manual, $2^{nd}$ edition, Cold Spring Harbor Laboratory, Cold Spring Harbor Laboratory Press, Cold Spring Harbor, N.Y., 1989.

In a further embodiment of the process, the ω-3-desaturases, Δ9-elongases, Δ6-desaturases, Δ8-desaturases, Δ6-elongases, Δ5-desaturases, Δ5-elongases and/or Δ4-desaturases can be expressed in single-cell plant cells (such as algae), see Falciatore et al., 1999, Marine Biotechnology 1 (3):239-251 and the references cited therein, and plant cells from higher plants (for example Spermatophytes, such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38.

A plant expression cassette preferably comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen et al., EMBO J. 3 (1984) 835 et seq.) or functional equivalents of these, but all other terminators which are functionally active in plants are also suitable.

Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie et al., 1987, Nucl. Acids Research 15:8693-8711).

As described above, plant gene expression must be functionally linked to a suitable promoter which performs the expression of the gene in a timely, cell-specific or tissue-specific manner. Promoters which can be used are constitutive promoters (Benfey et al., EMBO J. 8 (1989) 2195-2202) such as those which are derived from plant viruses such as 35S CAMV (Franck et al., Cell 21 (1980) 285-294), 19S CaMV (see also U.S. Pat. No. 5,352,605 and WO 84/02913) or plant promoters such as the promoter of the Rubisco small subunit, which is described in U.S. Pat. No. 4,962,028.

Other preferred sequences for the use in functional linkage in plant gene expression cassettes are targeting sequences which are required for targeting the gene product into its relevant cell compartment (for a review, see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells.

As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable promoters, for example the pathogen-induced PRP1-gene promoter (Ward et al., Plant Mol. Biol. 22 (1993) 361-366), the heat-inducible hsp80 promoter from tomato (U.S. Pat. No. 5,187,267), the cold-inducible alpha-amylase promoter from potato (WO 96/12814) or the wound-inducible pinII promoter (EP-A-0 375 091).

The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein et al., Mol. Gen. Genet., 1991, 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable promoters to be taken into consideration are the lpt2 or lpt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the sorghum kasirin gene, the rye secalin gene).

In particular, the multiparallel expression of the ω-3-desaturases, Δ9-elongases, Δ6-desaturases, Δ8-desaturases, Δ6-elongases, Δ5-desaturases, Δ5-elongases and/or Δ4-desaturases used in the process may be desired. Such expression cassettes can be introduced via a simultaneous transformation of a plurality of individual expression constructs or, preferably, by combining a plurality of expression cassettes on one construct. Also, it is possible to transform a plurality of vectors with in each case a plurality of expression cassettes and to transfer them to the host cell.

Likewise especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

Vector DNA can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J.

Host cells which are capable, in principle, of taking up the nucleic acid according to the invention, the gene product according to the invention or the vector according to the invention are all prokaryotic or eukaryotic organisms. The host organisms which are advantageously used are microorganisms such as fungi or yeasts, or plant cells, preferably plants or parts thereof. Fungi, yeasts or plants are used by preference, especially preferably plants, very especially preferably plants such as oil crops which comprise large amounts of lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassava, pepper, Tagetes, Solanaceae plants such as potato, tobacco, eggplant and tomato, *Vicia* species, pea, alfalfa, bushy plants (coffee, cacao, tea), *Salix* species, trees (oil palm, coconut) and perennial grasses and fodder crops. Especially preferred plants according to the invention are oil crops such as soybean, peanut, oilseed rape, canola, linseed, hemp, evening primrose, sunflower, safflower, trees (oil palm, coconut).

As described above, a further subject matter according to the invention are an isolated nucleic acid sequence which encodes polypeptides with ω-3-desaturase activity where the ω-3-desaturases encoded by the nucleic acid sequences converts $C_{18}$-, $C_{20}$- and $C_{22}$-fatty acids with two, three, four or five double bonds and advantageously polyunsaturated $C_{18}$-fatty acids with two or three double bonds and polyunsaturated $C_{20}$-fatty acids with two, three or four double bonds. $C_{22}$-Fatty acids with four or five double bonds are also desaturated.

In an advantageous embodiment, the term "nucleic acid (molecule)" as used in the present text additionally comprises the untranslated sequence at the 3' and at the 5' terminus of the coding gene region: at least 500, preferably 200, especially preferably 100 nucleotides of the sequence upstream of the 5' terminus of the coding region and at least 100, preferably 50, especially preferably 20 nucleotides of the sequence downstream of the 3' terminus of the coding gene region. An "isolated" nucleic acid molecule is separated from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' termini of the nucleic acid).

In various embodiments, the isolated ω-3-desaturase molecule can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived.

The nucleic acid molecules used in the process, for example a nucleic acid molecule with a nucleotide sequence of SEQ ID NO: 1 or part thereof, can be isolated using standard techniques of molecular biology and the sequence information provided herein. Also, for example a homologous sequence or homologous, conserved sequence regions at the DNA or amino acid level can be identified with the aid of comparative algorithms. These sequence regions can be used as hybridization probe and standard hybridization techniques (such as, for example, described in Sambrook et al., Molecular Cloning: A Laboratory Manual, $2^{nd}$ ed., Cold Spring Harbor Laboratory, Cold Spring Harbor Laboratory Press, Cold Spring Harbor, N.Y., 1989) for isolating further nucleic acid sequences which are useful in the process. Moreover, a nucleic acid molecule comprising a complete sequence of SEQ ID NO: 1 or part thereof can be isolated by polymerase chain reaction, where oligonucleotide primers which on the basis of this sequence or parts thereof are used (for example, a nucleic acid molecule comprising the complete sequence or part thereof can be isolated by polymerase chain reaction using oligonucleotide primers which have been generated on the basis of this very sequence). For example, mRNA can be isolated from cells (for example by the guanidinium thiocyanate extraction process by Chirgwin et al. (1979) Biochemistry 18:5294-5299) and cDNA can be generated by means of reverse transcriptase (for example Moloney-MLV reverse transcriptase, from Gibco/BRL, Bethesda, Md., or AMV reverse transcriptase, from Seikagaku America, Inc., St. Petersburg, Fla.). Synthetic oligonucleotide primers for the amplification by means of polymerase chain reaction can be generated on the basis of the sequence shown in SEQ ID NO: 1 or with the aid of the amino acid sequence shown in SEQ ID NO: 2. In accordance with the invention a nucleic acid can be amplified in accordance with standard PCR amplification techniques using cDNA or, alternatively, genomic DNA as template and suitable oligonucleotide primers. The nucleic acid amplified thus can be cloned into a suitable vector and characterized by means of DNA sequence analysis. Oligonucleotides which correspond to a desaturase nucleotide sequence can be generated by synthetic standard methods, for example using an automatic DNA synthesizer.

Homologs of the ω-3-desaturase nucleic acid sequence used, with the sequence SEQ ID NO: 1, mean for example allelic variants with at least 60%, preferably at least 70%, more preferably at least 80%, 90% or 95% and even more preferably at least approximately 95%, 96%, 97%, 98%, 99% or more identity or homology with a nucleotide sequence shown in SEQ ID NO: 1 or its homologs, derivatives or analogs or parts thereof. Furthermore, homologs are isolated nucleic acid molecules of a nucleotide sequence which hybridize, for example under stringent conditions, with the nucleotide sequence shown in SEQ ID NO: 1 or a part thereof. Allelic variants comprise in particular functional variants which can be obtained by deletion, insertion or substitution of nucleotides from/into the sequence shown in SEQ ID NO: 1, the intention being, however, that the enzyme activity of the resulting proteins synthesized advantageously being retained for the insertion of one or more genes. Proteins which still retain the enzmatic activity of ω-3-desaturase, i.e. whose activity is essentially not reduced, mean proteins with at least 10%, preferably 20%, especially preferably 30%, very especially preferably 40% of the original enzyme activity in comparison with the protein encoded by SEQ ID NO: 1. The homology was calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981))], which are part of the GCG software packet [Genetics Computer Group, 575 Science Drive, Madison, Wis., USA 53711 (1991)], were used. The sequence homology values detailed above in percent were determined using the program GAP over the entire sequence region with the following settings: Gap Weight: 50, Length Weight: 3, Average Match: 10.000 and Average Mismatch: 0.000, which, unless otherwise specified, were always used as standard settings for sequence alignments.

Homologs of SEQ ID NO: 1 also mean for example bacterial, fungal and plant homologs, truncated sequences, single-stranded DNA or RNA of the coding and noncoding DNA sequence.

Homologs of SEQ ID NO: 1 also mean derivatives such as, for example, promoter variants. The promoters upstream of the nucleotide sequences stated can be modified by one or more nucleotide substitutions, by insertion(s) and/or deletion(s), without, however, the functionality or activity of the promoters being adversely affected. Furthermore, it is possible that the activity of the promoters is increased by modifying their sequence, or that they are replaced completely by more active promoters, including those from heterologous organisms.

The abovementioned nucleic acids and protein molecules with ω-3-desaturase activity which are involved in the metabolism of lipids and fatty acids, PUFA cofactors and enzymes or in the transport of lipophilic compounds across membranes are used in the process according to the invention for modulating the production of PUFAs in transgenic organisms, advantageously in plants such as maize, wheat, rye, oats, triticale, rice, barley, soybean, peanut, cotton, *Linum* species such as linseed or flax, *Brassica* species such as oilseed rape, canola and turnip, pepper, sunflower, borage, evening primrose and Tagetes, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops either directly (for example when the overexpression or optimization of a fatty acid biosynthetic protein has a direct effect on the yield, production and/or production efficiency of the fatty acid from modified organisms) and/or can have an indirect effect which nevertheless entails an increase in the yield, production and/or production efficiency of the PUFAs or a decrease of undesired compounds (for example when the modulation of the metabolism of lipids and fatty acids, cofactors and enzymes results in changes in the yield, production and/or production efficiency or the composition of the desired compounds within the cells which, in turn, can have an effect on the production of one or more fatty acids).

The combination of a variety of precursor molecules and biosynthetic enzymes leads to the production of different fatty acid molecules, which has a major effect on the composition of the lipids since polyunsaturated fatty acids (=PUFAs) are incorporated not only simply into triacylglycerol but also into membrane lipids.

Boraginaceae, Primulaceae or Linaceae are especially suitable for the production of PUFAs, for example stearidonic acid, eicosapentaenoic acid or docosahexaenoic acid. Especially advantageously suitable for the production of PUFAs with the nucleic acid sequences according to the invention, advantageously, as described, in combination with further desaturases and elongases, is flax (*Linum usitatissimum*).

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After condensation reaction, these two product molecules together form acetoacetyl-ACP, which is converted via a series of condensation, reduction and dehydration reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., p. 612-636 and references cited therein; Lengeler et al. (Ed.) (1999) Biology of Procaryotes. Thieme: Stuttgart, New York, and the references therein, and Magnuson, K., et al. (1993) Microbiological Reviews 57:522-542 and the references therein). To undergo the further elongation steps, the resulting phospholipid-bound fatty acids must then be returned from the phospholipids to the fatty acid CoA ester pool. This is made possible by acyl-CoA:lysophospholipid acyltransferases. Moreover, these enzymes are capable of transferring the elongated fatty acids from the CoA esters back to the phospholipids. If appropriate, this reaction sequence can be followed repeatedly.

Examples of precursors for PUFA biosynthesis are oleic acid, linoleic acid and linolenic acid. These $C_{18}$-carbon fatty acids must be elongated to $C_{20}$ and $C_{22}$ to obtain fatty acids of the eicosa and docosa chain type. It is possible, with the aid of the ω-3-desaturase used in the process, to convert arachidonic acid into eicosapentaenoic acid and docosapentaenoic acid into docosahexaenoic acid and subsequently to use them for a variety of purposes in applications in the fields of foodstuffs, feedstuffs, cosmetics or pharmaceuticals. Using the abovementioned enzymes, $C_{18}$-, $C_{20}$- and/or $C_{22}$-fatty acids with at least two, advantageously at least three, four, five or six double bonds in the fatty acid molecule, preferably $C_{20}$- or $C_{22}$-fatty acids with advantageously four, five or six double bonds in the fatty acid molecule, can be produced. The desaturation can take place before or after elongation of the fatty acid in question. This is why the products of the desaturase activities and the further possible desaturation and elongation lead to preferred PUFAs with a higher degree of desaturation, including a further elongation of $C_{20}$- to $C_{22}$-fatty acids. Substrates of the desaturase used in the process according to the invention are $C_{18}$-, $C_{20}$- or $C_{22}$-fatty acids such as, for example, linoleic acid, γ-linolenic acid, dihomo-γ-linolenic acid, arachidonic acid, docosatetraenoic acid or docosapentaenoic acid. Preferred substrates are arachidonic acid, docosatetraenoic acid or docosapentaenoic acid. The synthesized $C_{20}$- or $C_{22}$-fatty acids with at least two, double bonds in the fatty acid are obtained in the process according to the invention in the form of the free fatty acid or in the form of its esters, for example in the form of its glycerides.

The term "glyceride" is understood as meaning glycerol esterified with one, two or three carboxyl radicals (mono-, di- or triglyceride). "Glyceride" is also understood as meaning a mixture of various glycerides. The glyceride or glyceride mixture can comprise further additions, for example free fatty acids, antioxidants, proteins, carbohydrates, vitamins and/or other substances.

A "glyceride" for the purposes of the process according to the invention is furthermore understood as meaning derivatives which are derived from glycerol. In addition to the above-described fatty acid glycerides, these also include glycerophospholipids and glyceroglycolipids. Preferred examples which may be mentioned here are the glycerophospholipids such as lecithin (phosphatidylcholine), cardiolipin, phosphatidylglycerol, phosphatidylserine and alkylacylglycerophospholipids.

Furthermore, fatty acids must subsequently be transported to various sites of modification and incorporated into the triacylglycerol storage lipid. A further important step in lipid synthesis is the transfer of fatty acids onto the polar head groups, for example by glycerol-fatty-acid acyltransferase (see Frentzen, 1998, Lipid, 100 (4-5):161-166).

For publications on plant fatty acid biosynthesis, desaturation, the lipid metabolism and the membrane transport of fatty compounds, beta-oxidation, fatty acid modification and cofactors, triacylglycerol storage and assembly, including the references therein, see the following articles: Kinney, 1997, Genetic Engineering, Ed.: JK Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: JK Setlow, 18:111-13; Gerhardt, 1992, Prog. Lipid R. 31:397-417; Guhnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantity and must therefore take up additionally, although they can be readily synthesized by other organisms such as bacteria; for example, cats are no longer capable of synthesizing arachidonic acid.

Phospholipids which are advantageously converted by the ω-3-desaturase according to the invention are to be understood as meaning, for the purposes of the invention, phosphatidylcholine, phosphatidylethanolamine, phosphatidylserine, phosphatidylglycerol and/or phosphatidylinositol, advantageously phosphatidylcholine. The terms "production" or "productivity" are known in the art and refer to the concentration of the fermentation product (compounds of the formula I) formed within a certain period of time and a certain fermentation volume (for example kg of product per hour per liter). The term "production efficiency" comprises the time required for obtaining a certain amount of product (for example the time required by the cell for establishing a certain throughput rate of a fine chemical). The term "yield" or "product/carbon yield" is known in the art and comprises the efficiency of the conversion of the carbon source into the product (i.e. the fine chemical). This is usually expressed for example as kg of product per kg of carbon source. By increasing the yield or production of the compound, the amount of the obtained molecules or of the suitable obtained molecules of this compound in a certain amount of culture is increased over a specified period. The terms "biosynthesis" or "biosynthetic pathway" are known in the art and comprise the synthesis of a compound, preferably of an organic compound, by a cell starting from intermediates, for example in a multistep process which is highly regulated. The terms "catabolism" or "catabolic pathway" are known in the art and comprise the cleavage of a compound, preferably of an organic compound, by a cell to give catabolytes (in more general terms, smaller or less complex molecules), for example in a multistep process which is highly regulated. The term "metabolism" is known in the art and comprises the totality of the biochemical reactions which take place in an organism. Thus, the metabolism of a certain compound (for example the metabolism of a fatty acid) comprises the totality of the biosynthetic, modification and catabolic pathways of this compound in the cell, which relate to this compound.

In addition to the ω-3-desaturases shown in SEQ ID NO: 1, the skilled worker recognizes that DNA sequence polymorphisms which lead to changes in the amino acid sequences of the ω-3-desaturase may exist within a population. These genetic polymorphisms in the ω-3-desaturase gene may exist between individuals within one population as the result of natural variation. These natural variants usually cause a variance of 1 to 5% in the nucleotide sequence of the ω-3-desaturase gene. All and sundry of these nucleotide variations and resulting amino acid polymorphisms in the ω-3-desaturase which are the result of natural variation and which do not change the functional activity shall be covered by the scope of the invention.

Nucleic acids molecules which are advantageous for the process according to the invention can be isolated on the basis of their homology with the ω-3-desaturase nucleic acids disclosed herein, using the sequences or part thereof as hybridization probe in accordance with standard hybridization techniques under stringent hybridization conditions. In this context, for example, it is possible to use isolated nucleic acid molecules which have a length of at least 15 nucleotides and which hybridize under stringent conditions with the nucleic acid molecules which comprise a nucleotide sequence of SEQ ID NO: 1. Nucleic acids which have at least 25, 50, 100, 250 or more nucleotides may also be used. The term "hybridizes under stringent conditions" as used in the present context is intended to describe hybridization and wash conditions under which nucleotide sequences which have at least 60% homology with one another usually remain hybridized with one another. The conditions are preferably such that sequences which have at least 65%, more preferably at least approximately 70% and even more preferably at least approximately 75% or more homology with one another usually remain hybridized with one another. These stringent conditions are known to the skilled worker and can be found in Current Protocols in Molecular Biology, John Wiley & Sons, N.Y. (1989), 6.3.1-6.3.6. A preferred, nonlimiting example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

To determine the percentage homology (=identity) of two amino acid sequences (for example the sequence SEQ ID NO: 2) or of two nucleic acids (for example SEQ ID NO: 1), the sequences are written one under the other for the purposes of optimal comparison (for example, gaps may be introduced into the sequence of a protein or of a nucleic acid in order to bring about an optimal alignment with the other protein or the other nucleic acid). The amino acid residues or nucleotides at the corresponding amino acid positions or nucleotide positions are then compared. If a position in one sequence is occupied by the same amino acid residue or the same nucleotide as the corresponding position in the other sequence, the molecules are homologous at this position (i.e, amino acid or nucleic acid "homology" as used in the present context corresponds to amino acid or nucleic acid "identity"). The percentage homology between the two sequences is a function of the number of identical positions which the sequences share (i.e. % homology=number of identical positions/total number of positions×100). The terms homology and identity can thus be regarded as being synonymous. The programs and algorithms used are described above.

An isolated nucleic acid molecule which codes for an ω-3-desaturase and which is homologous to the protein sequence of SEQ ID NO: 2 can be generated by introducing one or more nucleotide substitutions, additions or deletions into a nucleotide sequence of SEQ ID NO: 1, so that one or more amino acid substitutions, addition or deletions are introduced into the encoded protein. Mutations can be introduced into one of the sequence of SEQ ID NO: 1 by standard techniques, such as site-specific mutagenesis and PCR-mediated mutagenesis. It is preferred to generate conservative amino acid substitutions at one or more of the predicted nonessential amino acid residues. In a "conservative amino acid substitution", the amino acid residue is exchanged for an amino acid residue with a similar side chain. Families of amino acid residues with similar side chains have been defined in the art. These families comprise amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in a lysophosphatidic acid acyltransferase, glycerol-3-phosphate acyltransferase, diacylglycerol acyltransferase or lecithin cholesterol acyltransferase is thus preferably exchanged for another amino acid residue from the same side-chain family. As an alternative, in another embodiment, the mutations can be introduced randomly over the entire sequence coding for lysophosphatic acid acyltransferase, glycerol-3-phosphate acyltransferase, diacylglycerol acyltransferase or lecithin cholesterol acyltransferase or a part of this sequence, for example by saturation mutagenesis, and the resultant mutants can be screened for the lysophosphatidic acid acyltransferase, glycerol-3-phosphate acyltransferase, diacylglycerol acyltransferase or lecithin cholesterol acyltransferase activity described here, in order to identify mutants which have retained the lysophosphatidic acid acyltransferase, glycerol-3-phosphate acyltransferase, diacylglycerol acyltransferase or lecithin cholesterol acyltransferase activity. After the mutagenesis of one of the sequences of SEQ ID NO: 1, the protein encoded can be expressed recombinantly, and the activity of the protein can be determined for example using the assays described herein.

The invention furthermore relates to transgenic nonhuman organisms which comprise the nucleic acids SEQ ID NO: 1 according to the invention or a gene construct or a vector which comprise these nucleic acid sequences according to the invention. The nonhuman organism is preferably a microorganism, a nonhuman animal or a plant, especially preferably a plant.

This invention is illustrated in greater detail by the examples which follow, which are not to be construed as limiting. The content of all of the references, patent applications, patents and published patent applications cited in the present patent application is herewith incorporated by reference.

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the process of Sanger (Sanger et al. (1977) Proc. Natl. Acad. Sci. USA 74, 5463-5467). Fragments resulting from a polymerase chain reaction were sequenced and verified to avoid polymerase errors in constructs to be expressed.

Example 3

Cloning the ω-3-Specific Desaturase from *Phytophthora infestans*

As the result of a search for conserved regions in the protein sequences corresponding to the desaturase genes detailed in the description, one sequence with suitable motifs characteristic of a desaturase was identified in an EST sequence database.

| Name of gene | Genbank No. | Amino acids |
|---|---|---|
| Pi-omega3Des | SEQ ID NO: 1 | 361 |

Total RNA from *Phytophthora infestans* was isolated with the aid of the RNAeasy Kit from Qiagen (Valencia, Calif., US) and used for establishing an EST sequence database. Poly-A+ RNA (mRNA) was isolated from the total RNA with the aid of oligo-dT cellulose (Sambrook et al., 1989). The RNA was subjected to reverse transcription using the reverse transcription system kit from Promega, and the cDNA synthesized was cloned into the lambda ZAP vector (lambda ZAP Gold, Stratagene). The cDNA was depackaged in accordance with the manufacturer's instructions to give the plasmid DNA. The cDNA plasmid library was then used for the PCR for cloning expression plasmids. The sequence data were deposited in a suitable database.

Example 4

Cloning an Expression Plasmid to Express the Pi-Omega3Des Heterologously in Yeast To express the Pi-omega3Des clone heterologously in yeast, the former was cloned by PCR into the yeast expression vector pYES3, using suitable Pi-omega3Des-specific primers. In doing so, exclusively the gene's open reading frame which codes for the Pi-omega3Des protein was amplified and provided with two cleavage sites for cloning into the expression vector pYES3:

```
                                        (SEQ ID NO: 3)
Forward Primer: 5'-TAAGCTTACATGGCGACGAAGGAGG (SEQ ID NO: 4)
Reverse Primer: 5'-TGGATCCACTTACGTGGACTTGGT
```

Composition of the PCR mixture (50 μl):
5.00 μl template cDNA
5.00 μl 10× buffer (Advantage polymerase)+25 mM $MgCl_2$
5.00 μl 2 mM dNTP
1.25 μl per primer (10 μmol/μl of the 5'-ATG and of the 3'-stop primer)
0.50 μl Advantage polymerase
The Advantage polymerase employed was from Clontech.
PCR Reaction Conditions:
Annealing temperature: 1 min 55° C.
Denaturation temperature: 1 min 94° C.
Elongation temperature: 2 min 72° C.
Number of cycles: 35

The PCR product was incubated for 2 hours at 37° C. with the restriction enzymes HindIII and BamHI. The yeast expression vector pYES3 (Invitrogen) was incubated in the same manner. Thereafter, the 1104 bp PCR product and the vector were separated by agarose gel electrophoresis and the corresponding DNA fragments were excised. The DNA was purified by means of the Qiagen Gel Purification Kit following the manufacturer's instructions. Thereafter, the vector and the desaturase cDNA were ligated. The Rapid Ligation Kit from Roche was used for this purpose. The resulting plasmid pYES3-Pi-omega3Des was verified by sequencing and transformed into the *Saccharomyces* strain INVSc1 (Invitrogen) by means of electroporation (1500 V). As a control, pYES3 was transformed in parallel. Thereafter, the yeasts were plated onto complete tryptophan minimal medium with 2% glucose. Cells which were capable of growing even without tryptophan in the medium thus comprise the corresponding plasmids pYES3, pYES3-Pi-omega3Des. After the selection, in each case two transformants were selected for the further functional expression.

Example 5

Cloning Expression Plasmids for the Seed-Specific Expression in Plants

To transform plants, a further transformation vector based on pSUN-USP was generated. To this end, NotI cleavage sites were introduced at the 5' and 3' termini of the coding sequence using the following primer pair:
pSUN-Pi-omega3Des (SEQ ID NO: 5)
Reverse: 3'-GCGGCCGCTTACGTGGACTTGGTC (SEQ ID NO: 6)
Forward: 5'-GCGGCCGCatGGCGACGAAGGAGG Composition of the PCR mixture (50 µl):
5.00 µl template cDNA
5.00 µl 10× buffer (Advantage polymerase)+25 mM MgCl$_2$
5.00 µl 2 mM dNTP
1.25 µl per primer (10 µmol/µl)
0.50 µl Advantage polymerase
The Advantage polymerase employed was from Clontech.
PCR Reaction Conditions:
Annealing temperature: 1 min 55° C.
Denaturation temperature: 1 min 94° C.
Elongation temperature: 2 min 72° C.
Number of cycles: 35

The PCR products were incubated with the restriction enzyme NotI for 4 hours at 37° C. The plant expression vector pSUN300-USP was incubated in the same manner. Thereafter, the PCR products and the 7624 bp vector were separated by agarose gel electrophoresis, and the corresponding DNA fragments were excised. The DNA was purified by means of the Qiagen Gel Purification Kit following the manufacturer's instructions. Thereafter, vector and PCR products were ligated. The Rapid Ligation Kit from Roche was used for this purpose. The resulting plasmid pSUN-Pi-omega3Des was verified by sequencing.

Example 6

Expression of Pi-omega3Des in Yeasts

Yeasts which had been transformed with the plasmid pYES3 or pYES3-Pi-omega3Des as described in Example 4 were analyzed as follows:
The yeast cells from the main cultures were harvested by centrifugation (100×g, 5 min, 20° C.) and washed with 100 mM NaHCO$_3$, pH 8.0 in order to remove a residual medium and fatty acids. Fatty acid methyl esters (FAMEs) were prepared from the yeast cell sediments by acid methanolysis. To this end, the cell sediments were incubated for 1 hour at 80° C. with 2 ml of 1 N methanolic sulfuric acid and 2% (v/v) dimethoxypropane. The FAMEs were extracted by twice extracting with petroleum ether (PE). To remove non-derivatized fatty acids, the organic phases were washed in each case once with 2 ml of 100 mM NaHCO$_3$, pH 8.0, and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph with flame ionization detector. The conditions for the GLC analysis were as follows: the oven temperature was programmed from 50° C. to 250° C. with an increment of 5° C./min and finally 10 minutes at 250° C. (holding). The signals were identified by comparing the retention times with corresponding fatty acid standards (Sigma). The methodology is described for example in Napier and Michaelson, 2001, Lipids 36(8):761-766; Sayanova et al., 2001, Journal of Experimental Botany, 52(360):1581-1585, Sperling et al., 2001, Arch. Biochem. Biophys. 388(2):293-298 and Michaelson et al., 1998, FEBS Letters. 439(3):215-218.

Example 7

Functional Characterization of Pi-Omega3Des

The substrate specificity was determined after expression and feeding with various fatty acids (FIGS. 2 to 8). The fed substrates are present in large amounts in all transgenic yeasts, which proves the uptake of these fatty acids into the yeasts. The transgenic yeasts show that new fatty acids have been synthesized, the products of the Pi-omega3Des reaction. This means that the gene Pi-omega3Des was expressed functionally.

FIG. 2 shows the desaturation of linoleic acid (18:2 ω-6-fatty acid) to α-linolenic acid (18:3 ω-3-fatty acid) by Pi-omega3Des. The fatty acid methyl esters are synthesized by subjecting intact cells which had been transformed with the blank vector pYES2 (FIG. 2 A) or the vector pYes3-Pi-omega3Des (FIG. 2 B) to acid methanolysis. The yeasts were grown in minimal medium in the presence of C18:2$^{\Delta 9,12}$-fatty acid (300 µM). The FAMEs were then analyzed via GLC.

FIG. 3 shows the desaturation of γ-linolenic acid (18:3 ω-6-fatty acid) to stearidonic acid (18:4 ω-3-fatty acid) by Pi-omega3Des. The fatty acid methyl esters are synthesized by subjecting intact cells which had been transformed with the blank vector pYES2 (FIG. 3 A) or the vector pYes3-Pi-omega3Des (FIG. 3 B) to acid methanolysis. The yeasts were grown in minimal medium in the presence of γ-C18:3$^{\Delta 6,9,12}$-fatty acid (300 µM). The FAMEs were then analyzed via GLC.

FIG. 4 shows the desaturation of C20:2 ω-6-fatty acid to C20:3 ω-3-fatty acid by Pi-omega3Des. The fatty acid methyl esters are synthesized by subjecting intact cells which had been transformed with the blank vector pYES2 (FIG. 4 A) or the vector pYes3-Pi-omega3Des (FIG. 4 B) to acid methanolysis. The yeasts were grown in minimal medium in the presence of C20:2$^{\Delta 11,14}$-fatty acid (300 µM). The FAMEs were then analyzed via GLC.

FIG. 5 shows the desaturation of C20:3 ω-6-fatty acid to C20:4 ω-3-fatty acid by Pi-omega3Des. The fatty acid methyl esters are synthesized by subjecting intact cells which had been transformed with the blank vector pYES2

(FIG. 5 A) or the vector pYes3-Pi-omega3Des (FIG. 5 B) to acid methanolysis. The yeasts were grown in minimal medium in the presence of C20:3$^{\Delta 8,11,14}$-fatty acid (300 µM). The FAMEs were then analyzed via GLC.

FIG. 6 shows the desaturation of arachidonic acid (C20:4 ω-6-fatty acid) to eicosapentaenoic acid (C20:5 ω-3-fatty acid) by Pi-omega3Des. The fatty acid methyl esters are synthesized by subjecting intact cells which had been transformed with the blank vector pYES2 (FIG. 6 A) or the vector pYes3-Pi-omega3Des (FIG. 6 B) to acid methanolysis. The yeasts were grown in minimal medium in the presence of C20:4$^{\Delta 5,8,11,14}$-fatty acid (300 µM). The FAMEs were then analyzed via GLC.

FIG. 7 shows the desaturation of docosatetraenoic acid (C22:4 ω-6-fatty acid) to docosapentaenoic acid (C22:5 ω-3-fatty acid) by Pi-omega3Des. The fatty acid methyl esters are synthesized by subjecting intact cells which had been transformed with the blank vector pYES2 (FIG. 7 A) or the vector pYes3-Pi-omega3Des (FIG. 7 B) to acid methanolysis. The yeasts were grown in minimal medium in the presence of C22:4$^{\Delta 10,13,16}$-fatty acid (300 µM). The FAMEs were then analyzed via GLC.

The substrate specificity of Pi-omega3Des with regard to various fatty acids can be seen from FIG. 8. The yeasts which have been transformed with the vector pYes3-Pi-omega3Des were grown in minimal medium in the presence of the fatty acids stated. The fatty acid methyl esters were synthesized by subjecting intact cells to acid methanolysis. The FAMEs were subsequently analyzed by GLC. Each value represents a mean from three measurements. The conversion rates (% desaturation) were calculated using the formula:

$$[product]/[product]+[substrate]*100.$$

Example 8

Lipid Extraction from Seeds

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of the desired product (i.e. of the lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research, Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for the production of the desired compound, such as intermediates and by-products, in order to determine the overall production efficiency of the compound. The analytical methods comprise measuring the amount of nutrients in the medium (for example sugars, hydrocarbons, nitrogen sources, phosphate and other ions), measuring the biomass composition and the growth, analyzing the production of conventional metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas liquid chromatography/mass spectrometry; TAG, triacylglycerol; TLC, thin-layer chromatography).

The unambiguous detection for the presence of fatty acid products can be obtained by analyzing recombinant organisms using analytical standard methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometry methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 m, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Plant material is initially homogenized mechanically by comminuting in a pestle and mortar to make it more amenable to extraction.

This is followed by heating at 100° C. for 10 minutes and, after cooling on ice, by resedimentation. The cell sediment is hydrolyzed for one hour at 90° C. with 1 M methanolic sulfuric acid and 2% dimethoxypropane, and the lipids are transmethylated. The resulting fatty acid methyl esters (FAMEs) are extracted in petroleum ether. The extracted FAMEs are analyzed by gas liquid chromatography using a capillary column (Chrompack, WCOT Fused Silica, CP-Wax-52 CB, 25 m, 0.32 mm) and a temperature gradient of from 170° C. to 240° C. in 20 minutes and 5 minutes at 240° C. The identity of the fatty acid methyl esters is confirmed by comparison with corresponding FAME standards (Sigma). The identity and position of the double bond can be analyzed further by suitable chemical derivatization of the FAME mixtures, for example to give 4,4-dimethoxyoxazolin derivatives (Christie, 1998) by means of GC-MS.

Example 9

Generation of Transgenic Plants a) Generation of Transgenic Oilseed Rape Plants (Modified Process of Moloney et al., 1992, Plant Cell Reports, 8:238-242)

Binary vectors in *Agrobacterium tumefaciens* C58C1: pGV2260 or *Escherichia coli* (Deblaere et al., 1984, Nucl. Acids. Res. 13, 4777-4788) were used for generating transgenic oilseed rape plants. To transform oilseed rape plants (Var. *Drakkar*, NPZ Nordeutsche Pflanzenzucht, Hohenlieth, Germany), a 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) was used. Petiols or hypocotyls of freshly germinated sterile oilseed rape plants (in each case approx. 1 cm$^2$) were incubated with a 1:50 agrobacterial dilution for 5-10 minutes in a petri dish. This is followed by 3 days of coincubation in the dark at 25° C. on 3MS medium supplemented with 0.8% Bacto agar. The cultures were then grown for 3 days at 16 hours light/8 hours dark. The cultivation is then continued in a weekly rhythm on MS medium supplemented with 500 mg/l Claforan (cefotaxime sodium), 50 mg/l kanamycin, 20 M benzylaminopurine (BAP) and 1.6 g/l of glucose. Growing shoots were transferred to MS medium supplemented with 2% sucrose, 250 mg/l Claforan and 0.8% Bacto agar. If no roots had developed after three weeks, 2-indolebutyric acid was added to the medium as growth hormone for rooting.

Regenerated shoots were obtained on 2MS medium supplemented with kanamycin and Claforan; after rooting, they were transferred to compost and, after growing for two weeks in a controlled-environment cabinet or in the greenhouse, allowed to flower, and mature seeds were harvested and analyzed by lipid analyses for ω-3-desaturase expression. In this manner, lines with elevated contents of polyunsaturated $C_{20}$- and $C_{22}$-fatty acids were identified.

b) Generation of Transgenic Linseed Plants

Transgenic linseed plants can be generated for example by the process of Bell et al., 1999, In Vitro Cell. Dev. Biol.-Plant. 35(6):456-465 by means of particle bombardment. *Agrobacteria*-mediated transformations can be effected for example by the process of Mlynarova et al. (1994), Plant Cell Report 13: 282-285.

Equivalents:

Many equivalents of the specific embodiments according to the invention described herein can be seen or found by the skilled worker by simple routine experiments. These equivalents are intended to be included in the patent claims.

We claim:

1. A transgenic nonhuman organism expressing a recombinant polypeptide having ω-3-desaturase activity, wherein said recombinant polypeptide is selected from the group consisting of:
   (a) a polypeptide encoded by a nucleic acid comprising the nucleic acid sequence of SEQ ID NO: 1;
   (b) a polypeptide comprising the amino acid sequence of SEQ ID NO: 2;
   (c) a polypeptide encoded by a nucleic acid having at least 70% sequence identity to the nucleic acid sequence of SEQ ID NO: 1; and
   (d) a polypeptide having at least 70% sequence identity to the amino acid sequence of SEQ ID NO: 2.

2. The transgenic nonhuman organism of claim 1, wherein the organism is a microorganism, a nonhuman animal or a plant.

3. The transgenic nonhuman organism of claim 1, wherein the organism is a plant.

4. The transgenic nonhuman organism of claim 1, wherein the organism is an oil-producing plant, a vegetable producing plant or an ornamental plant.

5. A process for production of oils, lipids and/or fatty acids having an elevated content of ω-3 unsaturated fatty acids, comprising:
   (a) obtaining the transgenic nonhuman organism of claim 1; and
   (b) culturing the organism under conditions which permits the production of oils, lipids and/or fatty acids, wherein said transgenic nonhuman organism produces oils, lipids and/or fatty acids with an elevated content of ω-3 unsaturated fatty acids as compared to oils, lipids and/or fatty acids produced by a corresponding control organism without expressing said polypeptide.

6. The process of claim 5, wherein the oils, lipids and/or fatty acids produced in said transgenic nonhuman organism comprise an elevated content of ω-3 unsaturated fatty acids having more than three double bonds as compared to oils, lipids and/or fatty acids produced by a corresponding control organism without expressing said polypeptide.

7. The process of claim 5, further comprising isolating oils, lipids and/or fatty acids produced from said transgenic nonhuman organism.

8. The process of claim 5, wherein the transgenic nonhuman organism further expresses at least one polypeptide selected from the group consisting of Δ4-desaturase, Δ5-desaturase, Δ6 desaturase, Δ8-desaturase, Δ5-elongase, Δ6-elongase and Δ9-elongase gene.

9. An expression cassette comprising a nucleic acid molecule encoding a polypeptide having ω-3-desaturase activity, wherein said nucleic acid molecule is operably linked to one or more heterologous regulatory sequences, and wherein said polypeptide having ω-3-desaturase activity is selected from the group consisting of:
   (a) a polypeptide encoded by a nucleic acid comprising the nucleic acid sequence of SEQ ID NO: 1;
   (b) a polypeptide comprising the amino acid sequence of SEQ ID NO: 2;
   (c) a polypeptide encoded by a nucleic acid having at least 70% sequence identity to the nucleic acid sequence of SEQ ID NO: 1; and
   (d) a polypeptide having at least 70% sequence identity to the amino acid sequence of SEQ. ID NO: 2.

10. The process of claim 5, wherein the transgenic nonhuman organism is a plant, and wherein said process further comprises harvesting the plant after cultivation.

11. The process of claim 5, wherein the transgenic nonhuman organism is a plant, and wherein said process further comprises obtaining seeds from said plant.

12. The transgenic nonhuman organism of claim 1, wherein said recombinant polypeptide comprises:
   (a) an amino acid sequence having at least 80% sequence identity to the amino acid sequence of SEQ ID NO: 2; or
   (b) an amino acid sequence encoded by a nucleic acid sequence having at least 80% sequence identity to the nucleic acid sequence of SEQ ID NO: 1.

13. The transgenic nonhuman organism of claim 1, wherein said recombinant polypeptide is capable of desaturating ω-6 C20- and C22-fatty acids to ω-3 C20- and C22-fatty acids.

14. The transgenic nonhuman organism of claim 13, wherein said recombinant polypeptide is capable of desaturating ω-6 C20:2-, C20:3-, C20:4-, or C22:4-fatty acids.

15. The transgenic nonhuman organism of claim 13, wherein said recombinant polypeptide is additionally capable of desaturating ω-6 C18-fatty acids to ω-3 C18-fatty acids.

16. The transgenic nonhuman organism of claim 13, wherein said recombinant polypeptide is additionally capable of desaturating ω-6 C18:2- or C18:3-fatty acids.

17. The transgenic nonhuman organism of claim 13, wherein the ω-6 C20- or C22-fatty acids are bound at the sn1 and sn2 positions in phospholipids, and wherein said recombinant polypeptide is capable of desaturating said ω-6 C20- or C22-fatty acids to ω-3 C20- or C22-fatty acids.

18. The transgenic nonhuman organism of claim 13, wherein said recombinant polypeptide is capable of desaturating ω-6 C20- or C22-fatty acids bound at the sn1 and sn2 positions in phospholipids to ω-3 C20- or C22-fatty acids, and wherein said ω-6 C20-fatty acids are C20:4-fatty acids bound at the sn1 and sn2 positions in phospholipids.

19. The transgenic nonhuman organism of claim 13, wherein said recombinant polypeptide is capable of desaturating ω-6 C20- or C22-fatty acids in phosphatidylcholine (PC), phosphatidylinositol (PIS) and/or phosphatidylethanolamine (PE) to ω-3 C20- or C22-fatty acids.

20. The expression cassette of claim 9, wherein said polypeptide is capable of desaturating ω-6 C20- and C22-fatty acids to ω-3 C20- and C22-fatty acids.

21. The expression cassette of claim 20, wherein said polypeptide is additionally capable of desaturating ω-6 C18-fatty acids to ω-3 C18-fatty acids.

22. A plant or a microorganism comprising the expression cassette of claim 9.

23. A plant part, plant cell, or seed of the plant of claim 22, wherein the plant part, plant cell, or seed comprises said expression cassette.

* * * * *